(12) United States Patent
Soerens et al.

(10) Patent No.: US 6,967,261 B1
(45) Date of Patent: Nov. 22, 2005

(54) BANDAGE, METHODS OF PRODUCING AND USING SAME

(75) Inventors: Dave Allen Soerens, Neenah, WI (US); Sohail Malik, Roswell, GA (US)

(73) Assignee: Kimberly-Clark Worldwide, Neenah, WI (US)

(*) Notice: Subject to any disclaimer, the term of this patent is extended or adjusted under 35 U.S.C. 154(b) by 658 days.

(21) Appl. No.: 10/034,906

(22) Filed: Dec. 28, 2001

(51) Int. Cl.$^7$ ............................................... A61F 13/00
(52) U.S. Cl. ........................... 602/48; 602/41; 602/42; 602/43
(58) Field of Search ............................... 602/41–48, 1, 602/8, 52, 54, 56; 424/444–449; 604/304–308

(56) References Cited

U.S. PATENT DOCUMENTS

| | | |
|---|---|---|
| 2,510,993 A | 6/1950 | Meyer et al. |
| 3,328,259 A | 6/1967 | Anderson |
| 3,338,992 A | 8/1967 | Kinney |
| 3,341,394 A | 9/1967 | Kinney |
| 3,419,006 A | 12/1968 | King |

(Continued)

FOREIGN PATENT DOCUMENTS

| | | |
|---|---|---|
| CA | 756190 | 4/1967 |
| EP | 0206697 A2 | 12/1986 |
| EP | 0361722 B1 | 12/1993 |
| EP | 0992252 A2 | 4/2000 |
| EP | 1008330 A2 | 6/2000 |
| WO | 96/13282 | 5/1996 |
| WO | 97/28832 | 8/1997 |
| WO | 99/59647 | 11/1999 |
| WO | 00/12038 | 3/2000 |

OTHER PUBLICATIONS

Fwu–Long Mi et al., "Fabrication and characterization of a sponge–like asymmetric chitosan membrane as a wound dressing", *Biomaterials*, England, vol. 22, No. 2, Jan. 2001, pp. 165–173.

Taber's ® *Cyclopedic Medical Dictionary*, Edition 18, F.A. Davis Co., 1997, p. 1085.

(Continued)

*Primary Examiner*—Nicholas D. Lucchesi
*Assistant Examiner*—Lalita M. Hamilton
(74) *Attorney, Agent, or Firm*—Steven D. Flack; James B. Robinson

(57) ABSTRACT

A bandage of the type used on acute wounds, minor wounds, burn wounds and irritations, includes a first layer for covering the wound site and an area around the wound site, with the first layer including a top surface and bottom surface; a second layer over the first layer bottom surface, for absorbing exudates from the wound site; the second layer including a poly(ethyleneoxide)-based compound and a chitosan-based compound. A third layer is situated over the second layer, the third layer being of a perforated film, and wherein, at least one antimicrobial agent is associated with the bandage in a position where the antimicrobial agent will come in contact with the wound site, and which is transferable from the bandage to the wound site, upon contact with the wound site.

17 Claims, 2 Drawing Sheets

U.S. PATENT DOCUMENTS

| | | |
|---|---|---|
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,963,605 A | 6/1976 | Seabourn |
| 3,976,563 A | 8/1976 | Scalco |
| 4,100,324 A | 7/1978 | Anderson et al. |
| 4,147,775 A | 4/1979 | Schwartz et al. |
| 4,147,831 A | 4/1979 | Balinth |
| 4,192,299 A | 3/1980 | Sabatano |
| 4,291,136 A | 9/1981 | Keogh |
| 4,328,323 A | 5/1982 | Keogh |
| 4,340,563 A | 7/1982 | Appel et al. |
| 4,343,917 A | 8/1982 | Keogh |
| 4,353,997 A | 10/1982 | Keogh |
| 4,369,289 A | 1/1983 | Keogh |
| 4,408,011 A | 10/1983 | Barnabeo |
| 4,434,272 A | 2/1984 | Keogh |
| 4,440,907 A | 4/1984 | Keogh |
| 4,446,279 A | 5/1984 | Keogh |
| 4,474,769 A | 10/1984 | Smith |
| 4,489,029 A | 12/1984 | Keogh et al. |
| 4,493,924 A | 1/1985 | Rifi |
| 4,526,920 A | 7/1985 | Sakashita et al. |
| 4,526,930 A | 7/1985 | Keogh |
| 4,551,490 A | 11/1985 | Doyle et al. |
| 4,551,504 A | 11/1985 | Barnabeo |
| 4,575,535 A | 3/1986 | Keogh |
| 4,579,913 A | 4/1986 | Keogh |
| 4,593,071 A | 6/1986 | Keogh |
| 4,616,644 A | 10/1986 | Saferstein et al. |
| 4,659,700 A | 4/1987 | Jackson |
| 4,753,993 A | 6/1988 | Keogh |
| 4,767,820 A | 8/1988 | Keogh |
| 4,795,668 A | 1/1989 | Krueger et al. |
| 4,818,464 A | 4/1989 | Lau |
| 4,946,870 A | 8/1990 | Partain, III et al. |
| 4,950,709 A * | 8/1990 | Schlueter et al. |
| 5,047,476 A | 9/1991 | Keogh |
| 5,057,368 A | 10/1991 | Largman et al. |
| 5,069,970 A | 12/1991 | Largman et al. |
| 5,108,820 A | 4/1992 | Kaneko et al. |
| 5,112,919 A | 5/1992 | Furrer et al. |
| 5,158,555 A | 10/1992 | Porzilli |
| 5,277,976 A | 1/1994 | Hogle et al. |
| 5,336,552 A | 8/1994 | Strack et al. |
| 5,382,400 A | 1/1995 | Pike et al. |
| 5,389,728 A | 2/1995 | Prejean |
| 5,466,410 A | 11/1995 | Hills |
| 5,578,661 A * | 11/1996 | Fox et al. |
| 5,633,070 A | 5/1997 | Murayama et al. |
| 5,800,372 A | 9/1998 | Bell et al. |
| 5,823,983 A | 10/1998 | Rosofsky et al. |
| 6,020,071 A | 2/2000 | Watson |
| 6,054,523 A | 4/2000 | Braun et al. |

OTHER PUBLICATIONS

W. Malette, H. Quigley, R. Gaines, N. Johnson, W.Rainer, "Chitosan: A New Hemostatic", *Annals of Thoracic Surgery*, vol. 36, No. 1, 1983, pp. 55–58.

R. Muzzarelli, R. Tarsi, O. Filippini, E. Giovanetti, G. Biagini, P. Varaldo, "Antimicrobial Properties of N–Carboxybutyl Chitosan", *Antimicrobial Agents and Chemotherapy*, vol. 34, No. 10, Oct. 1990, pp. 2019–2023.

R. Muzzarelli, V. Baldassarre, F. Conti, P. Ferrara, G. Biagini, "Biological Activity of Chitosan: Ultrastructural Study", *Biomaterials*, vol. 9, May 1988, pp. 247–252.

A. Tokoro, N. Tatewaki, K. Suzuki, T. Mikami, S. Suzuki, "Growth–Inhibitory Effect of Hexa–N–Acetylchitohexaose and Chitohexaose Against Meth–A Solid Tumor", *Chem. Pharm. Bulletin*, vol. 36, 1988, p. 784–790.

Y. Machida, T. Nagai, K. Inouye, T. Sannan, *Chitin and Chitosan: Sources, Chemistry, Biochemistry, Physical Properties and Applications*, G. Skjak–Braek, T. Anthonsen, P. Sanford (Eds.), Elsevier Science Publishers Ltd., 1989, pp. 45–69, 101–118, 139–147, 567–576, 605–616, 657–669, 679–691.

R. Muzzarelli, C. Jeuniaux, G. Gooday, *Chitin in Nature and Technology*, Plenum Press, New York, 1986, pp. 435–460, pp. 507–512.

Y. Ohshima et al., "Clinical Application of Chitin Non–Woven Fabric as Wound Dressing", *European Journal of Plastic Surgery*, 1987, pp. 66–69.

*The Journal of the American Chemical Society*, vol. LXVII, Jul.–Dec. 1945, pp. 1184–1186.

P. Klokkevold, D. Lew, D. Ellis, C. Bertolami, "Effect of Chitosan on Lingual Hemostasis in Rabbits", *J. Oral Maxillofacial Surgery*, 1991, pp. 858–863.

J. Hokanson, P. Hayward, D. Carney, L. Phillips, M. Robson, "A Mathematical Model for the Analysis of Experimental Wound Healing Data", *Wounds*, vol. 3, No. 6, Nov./Dec. 1991, pp. 213–220.

J. Davidson, "Animal Models for Wound Repair", *Arch Dermatol Res.*, 290 (Suppl), 1998, pp. S1–S11.

J. Heggers et al., "Beneficial Effect on Aloe on Wound Healing in an Excisional Wound Model", *The Journal of Alternative and Complementary Medicine*, vol. 2, No. 2,, 1996, pp. 271–277.

K. Nishimura, I. Azuma, *Chitin Derivatives in Life Sciences*, S. Tokura, I. Azuma, (Eds.), Japan Chitin Soc., 1992, pp. 7–11.

Muzzarelli et al., "Chitosans and Other Polysaccharides as Wound Dressing Materials", *Biomedical and Biotechnological Advances*, S. Stivala, V. Crescenzi, S. Stivala (Eds.), Oct. 1988, pp. 77–88.

L. Illum, "Chitosan and Its Use as a Pharmaceutical Excipient", *Pharmaceutical Research*, vol. 15, Nov. 9, 1998, pp. 1326–1331.

D. Singh, A. Ray, "Biomedical Applications of Chitin, Chitosan, and Their Derivatives", *Rev Macromol. Chem Phys.*, C40(1), 2000, pp. 69–83.

K. Nishimura, C. Ishihara, S. Ukei, S. Tokura, I. Azuma, "Stimulation of Cytokine Production in Mice Using Deacetylated Chitin", *Vaccine*, vol. 4, Sep. 1986, pp. 151–156.

* cited by examiner

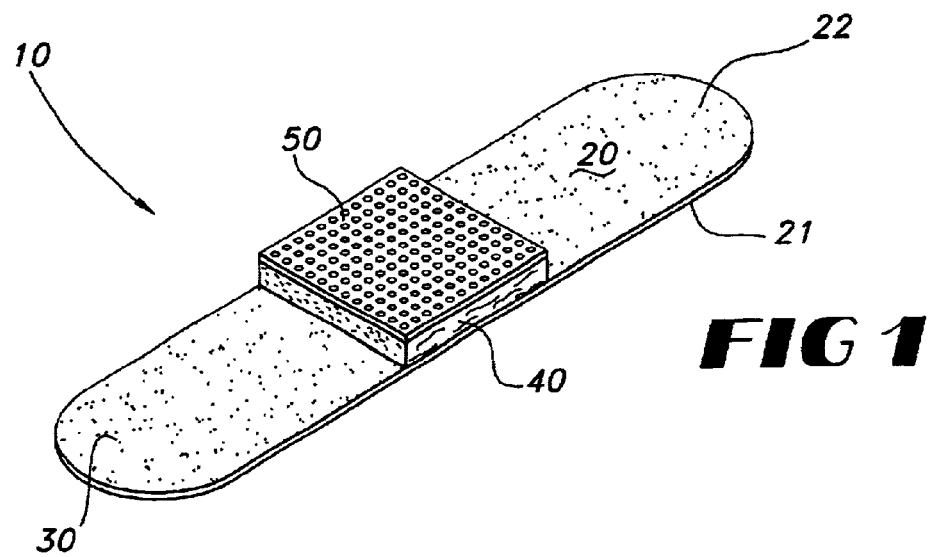
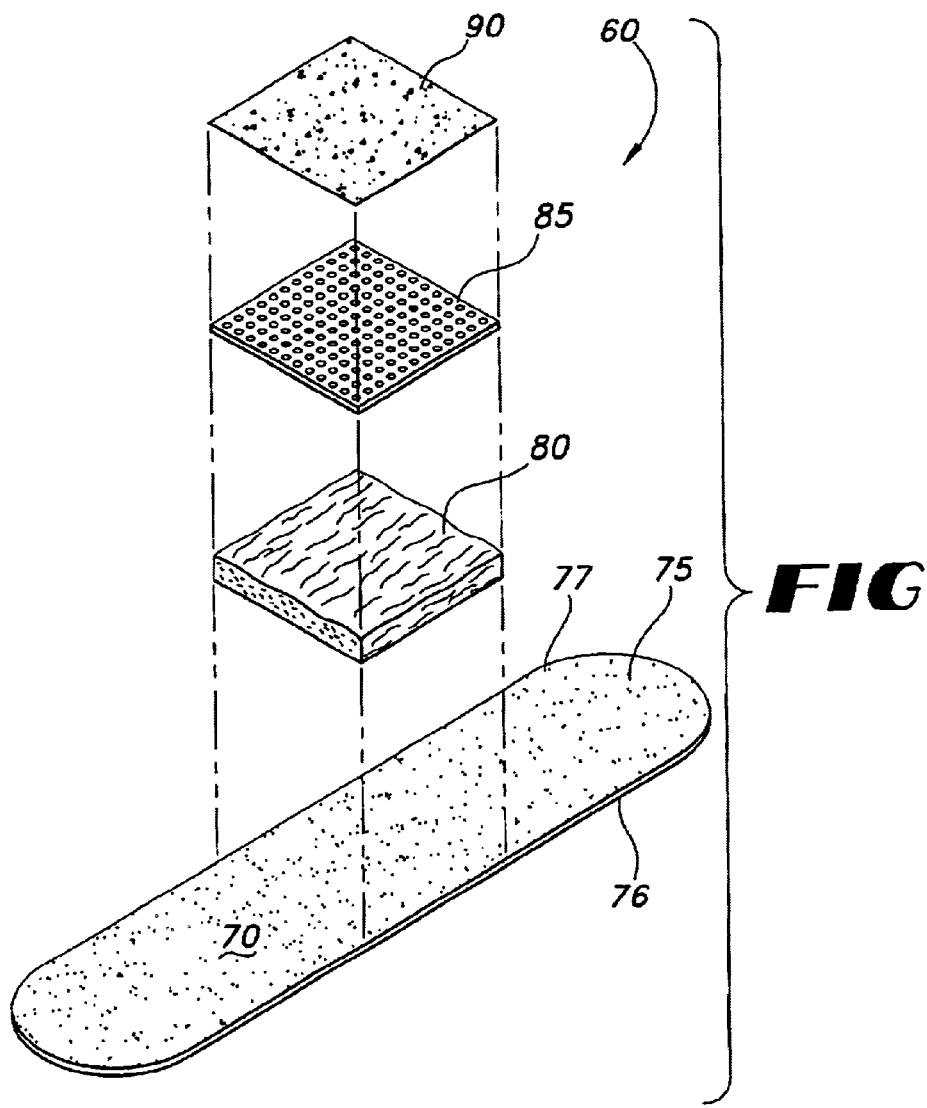

BANDAGE, METHODS OF PRODUCING AND USING SAME

FIELD OF THE INVENTION

The present invention relates to bandages/dressings for use by consumers. More particularly, the present invention relates to adhesive bandages and wound dressings for use by consumers, that promote wound healing, as well as methods of producing and using same.

BACKGROUND OF THE INVENTION

Adhesive bandages and wound dressings for use by the consumer to treat/dress acute wounds or skin irritations are not new. A seen in FIG. 1, such adhesive bandages 10 are generally passive, in that they offer little or no chemical treatment for wound healing. Rather, they primarily serve to exert low levels of pressure on the wound, protect the wound from exposure to the environment, and absorb any exudates, which are produced from the wound site.

Typically, such bandages include a base layer 20, which is the layer seen by the consumer following application of the bandage to the wound. Such layer is typically formed from a polymeric material such as a film, nonwoven web, or combination thereof, and may be perforated in some fashion to allow for flexibility and/or further breathability. Such layer often includes a film component, having a top side surface 21, which is seen by the consumer after application of the bandage to the wound site, and a bottom side surface (skin contacting surface) 22. A skin-friendly adhesive 30 is usually placed over the base layer bottom side surface to provide a means for attaching the bandage to the consumer. Alternatively, a separate adhesive tape is used to attach the bandage/wound dressing to the wound site, if the bandage/wound dressing is of the nonadhesive type. In the center of the base layer 20 bottom side surface 22 is traditionally positioned an absorbent pad 40 for absorbing exudates from the wound. Such absorbent pad is typically comprised of a nonwoven material, or alternatively a cellulosic wadding. The nonwoven material may be treated to be hydrophilic or may include superabsorbent materials. Finally, a non-stick perforated film layer 50 (exemplified by Delnet material) is normally positioned over the absorbent pad layer 40, to provide a barrier between the absorbent pad and the wound itself. This allows the wound fluid to move through the perforated layer without sticking to the wound site.

Such absorbent pads have provided some level of absorbency, however, since they often only hold fluid in pores between fibers, their ability to pull fluids from the surface of the wound is often compromised by limited capacity and by their inability to hold fluid when compressed. There is therefore a need for a bandage with an absorbent pad which continues to draw fluid from a wound after the bandage has remained on the wound, and which is capable of retaining or locking up fluid, even under compression, and which provides a moist environment for wound healing. There is a further need for a bandage absorbent pad, which demonstrates the ability to both pull fluid from a wound, but also to release a beneficial treatment agent to a wound. For the purposes of this application, the term "beneficial treatment agent" shall refer to a chemical agent that can be added to a bandage which actively promotes wound healing, such as for example, by providing an antimicrobial effect, or by providing a hemostatic effect to the wound site, or both. There is also a need for a bandage, which provides a multifunctional wound healing system utilizing one or more compounds.

Typically the absorbent pad in such bandage does not include any medicinal components, although comparatively recently, bandage manufacturers have started including antibiotic agents on or within bandages to encourage wound healing. Such agents may be coated on, or impregnated within the bandage. For instance, several products are currently being marketed which contain an antiseptic benzalkonium chloride and an antibiotic mixture of polymixin B-sulfate and bacitracin-zinc. Further, patents in this area of technology have described the use of commonly known antiseptics and antibiotics, such as those described in U.S. Pat. Nos. 4,192,299, 4,147,775, 3,419,006, 3,328,259, and 2,510,993. Unfortunately, certain individuals have proven to be allergic to antibiotics, and as such, these bandages cannot be freely used by all consumers. Furthermore, there has recently been a push in the medical community to avoid excessive use of antibiotics so as to eliminate the risk that certain bacteria may become resistant to such medications. There is therefore a need in the bandage field for a bandage that offers healing agents to a wound, that are not associated with allergic responses. That is, there is a need in the bandage/wound dressing field for a wound dressing which encourages rapid healing as well as retards bleeding and/or infection.

It has not been new for bandages to accomplish hemostatic functions. For instance, WO99/59647 describes a multilayered haemostatic bandage, which comprises preferably a thrombin layer between two fibrinogen layers. The dressing may contain other resorbable materials such as glycolic acid or lactic acid based polymers or copolymers. A hemostatic bandage is also disclosed in W0/97/28832. As in the previous reference, such bandage utilizes thrombin, in connection with fibrinogen, adhered to a fibrous matrix. While such bandages absorb fluid to a certain extent, they are directed to a hemostatic function.

U.S. Pat. No. 5,800,372 describes a field dressing for control of exsanguination. Such dressing describes the use of microfibrillar collagen and a superabsorbent polymer in a hemostatic bandage, which both absorbs blood and induces clotting. Such superabsorbent materials are fairly costly and significantly add to the cost of the wound dressing. Still further hemostatic bandages are disclosed in U.S. Pat. No. 4,616,644, and EP 0206697 A2, in which a thin coating of high molecular weight polyethyleneoxide is applied to the surface of a perforated plastic film wound release cover of an adhesive bandage. While such materials utilize polyethylene oxide in a bandage, such bandages do not appear to provide for the synergistic wound healing effect of such material with naturally occurring hemostatic and antimicrobial agents.

Poly(ethylene oxide) ("PEO") is one of a very few polymers that is both water-soluble and thermally processable. PEO has also been shown to be biodegradable under a variety of conditions. Initial work has been done with PEO N-80 (molecular weight~200,000) which is commercially available from Union Carbide. This grade of PEO is suitable for extrusion processing into film. However, the resultant films have relatively low tensile strength, low ductility, and brittleness. Typical values are 12 MPa break stress and elongation at break of 220%. In an unmodified form, high molecular weight PEO is not thermally processable. Melt fracture and excessive vaporization are observed as PEO is extruded. The resulting resins therefore cannot be cast into thin films, and do not have properties that are useful for bandage-type applications.

Additionally, recent development efforts have provided coating materials for a variety of uses. For example, U.S.

Pat. No. 6,054,523, to Braun et al., describes materials that are formed from organopolysiloxanes containing groups that are capable of condensation, a condensation catalyst, an organopolysiloxane resin, a compound containing a basic nitrogen, and polyvinyl alcohol. The materials are reported to be suitable for use as hydrophobic coatings and for paints and sealing compositions.

Others have reported the production of graft copolymers having silane functional groups that permitted the initiation of cross-linking by exposure to moisture. Prejean (U.S. Pat. No. 5,389,728) describes a melt-processible, moisture-curable graft copolymer that was the reaction product of ethylene, a 1–8 carbon alkyl acrylate or methacrylate, a glycidyl containing monomer such as glycidyl acrylate or methacrylate, onto which has been grafted N-tert-butylaminopropyl trimethoxysilane. The resulting copolymers were reported to be useful as adhesives and for wire and cable coatings, however.

Furrer et al. in U.S. Pat. No. 5,112,919, reported a moisture-crosslinkable polymer that was produced by blending a thermoplastic base polymer, such as polyethylene, or a copolymer of ethylene, with 1-butene, 1-hexene, 1-octene, or the like; a solid carrier polymer, such as ethylene vinylacetate copolymer (EVA), containing a silane, such as vinyltrimethoxysilane; and a free-radical generator, such as an organic peroxide; and heating the mixture. The copolymers could then be cross-linked by reaction in the presence of water and a catalyst, such as dibutyltin dilaurate, or stannous octoate.

U.S. Pat. No. 4,593,071 to Keough reported moisture cross-linkable ethylene copolymers having pendant silane acryloxy groups. The resultant cross-linked polymers were reported to be especially resistant to moisture and to be useful for extruded coatings around wires and cables. The same group has reported similar moisture curable polymers involving silanes in U.S. Pat. Nos. 5,047,476, 4,767,820, 4,753,993, 4,579,913, 4,575,535, 4,551,504, 4,526,930, 4,493,924, 4,489,029, 4,446,279, 4,440,907, 4,434,272, 4,408,011, 4,369,289, 4,353,997, 4,343,917, 4,328,323, and 4,291,136. Since the cured products of these formulations are reported to be useful for coverings for wire and cable, and for non-conductive coatings for electrical conductors, it would be expected that they are durable coatings for which properties such as water absorbency and biodegradability would be a disadvantage.

Water-swellable polymers have reportedly been produced by cross-linking water soluble polymers, such as poly(ethylene oxide). It is known that poly(alkylene oxides), such as poly(ethylene oxide), can be cross-linked through gamma irradiation. Depending upon the degree of irradiation and the degree of cross-linking, the properties of the cross-linked polymer can range from a water soluble material to a hard solid with no appreciable water absorbency. Materials that are substantially non-water soluble, but still absorbent can be made. However, the use of gamma rays requires expensive equipment and time consuming procedures due to safety concerns, and the degree of cross-linking that is obtained is often difficult to control.

Several references have reported the use of chemical cross-linking groups as a method of avoiding the dangers and costs associated with the use of ionizing radiation. U.S. Pat. No. 3,963,605 to Chu reported a water-swellable, cross-linked poly(alkylene oxide) that was produced by heating a mixture of poly(ethylene oxide) with acrylic acid and a free radical initiator such as acetyl peroxide in a hydrocarbon solvent such as hexane, heptane, or cyclohexane. Another alternative was reported in Canadian Pat. No. 756,190, and involved cross-linking through a di-vinyl monomer in the presence of a free radical catalyst. The use of other cross-linking agents, such as a diacrylate, or methyl-bis-acrylamide with a free radical inhibitor, have also been reported.

Lubricious coatings of cross-linked, hydrophilic polyurethane have been reported by Watson in U.S. Pat. No. 6,020,071. Another polyurethane coating is described by Tedeshchl et al., in EP 0992 252 A2, where a lubricious, drug-accommodating coating is described that is the product of a polyisocyanate; an amine donor, and/or a hydroxyl donor; and an isocyanatosilane adduct having terminal isocyanate groups and an alkoxy silane. A water soluble polymer, such as poly(ethylene oxide), can optionally be present. Cross-linking causes a polyurethane or a polyurea network to form, depending upon whether the isocyanate reacts with the hydroxyl donors or the amine donors. This composition provides lubricious benefits from a particular chemistry, which does not appear to provide high absorbency.

Chitosan is a deacetylated product of chitin $(C_8H_{13}NO_5)_n$, an abundant natural glucosamine polysaccharide found in the ecosystem. In particular, chitin is found in the shells of crustaceans, such as crabs, lobsters and shrimp. The compound is also found in the exoskeletons of marine zooplankton, in the wings of certain insects, such as butterflies and ladybugs, and in the cell wall of yeasts, mushrooms and other fungi.

In addition to being non-toxic, biocompatible and biodegradable, chitosan is also reported in the scientific literature to possess hemostatic, antimicrobial properties and other biomedical attributes. See for instance, *Rev Macromol. Chem Phys.*, C40, 69–83 (2000), *Chitin and Chitosan*, Editors, G. Skjak-Braek, T. Anthonsen and P. Sanford, Elsevier, (1988); *Chitin in Nature and Technology*, Editors, R. Muzzarelli, C. Jeuniaux and G. W. Gooday, Plenum Press, (1986).

The biocompatibility of chitosan administered orally and intravenously has been assessed in animals. Its $LD_{50}$ is over 16 g/Kg in mice, which is higher than for sucrose. $LD_{50}$ is traditionally defined as the median lethal dose of a substance, which will kill 50% of the animals receiving that dose, with the dose being calculated on amount of material given per gram or kilogram of body weight, or amount per unit of body surface area. See for instance, the $18^{th}$ Edition of *Taber's Cyclopedic Medical Dictionary*, p. 1085. The hemostatic properties of Chitosan have also been evaluated in the scientific literature in publications such as *Ann. Thor. Surg.*, 35, 55–60, (1983); *J Oral Maxillof Surg*, 49, 858–63, (1991).

In recent years, however, attention has been directed in the research community towards biomedical applications of the chitosan compound. In this regard, the use of chitosan in the pharmaceutical and healthcare industry is currently being evaluated. For instance, use of chitosan has been reported in a pharmaceutical product in *Pharm Res*, 15, 1326–31, (1998). The use of chitosan in the pharmaceutical industry as an excipient has also been explored in *Pharm Res*, 15, 1326–31, (1998) and *Drug Dev. Ind Pharm*, 24, 979–93, (1998).

Antimicrobial properties of chitosan have been reported against Gram positive and Gram negative bacteria, including Streptococcus spp., *Staphylococcus aureus, Staphylococcus epidermidis, Staphylococcus haemolyticus,* Pseudomonas, Escherichia, Proteus, Klebsiella, Serratia, Acinobacter, Enterobacter and Citrobacter spp. See for instance, Muzzarelli et al., in *Industrial Polysaccharides: Biomedical and Biotechnological Advances, Eds.*, V. Crescenzi and S. S. Stivala, Gordon and Breach, pp. 77–88, (1990) and *Antimicr. Agents Chemoth.*, 34, 2019–24, (1990). See also, U.S. Pat. No. 4,659,700, which describes the use of Chitosan in a gel to be applied to wounds.

Chitosan has also been described in the literature to induce repair of tissue containing regularly arranged collagen bundles. See for instance *Biomaterials*, 9, 247–52, (1988). Additionally, non-woven fabrics made of chitosan fibers have been developed. See for instance, *Eur. J. Plastic Surg.*, 10, 66–76, (1987). Further, chitin and chitosan derivatives have been studied for their antitumor effects. See for instance, *Carbohydr. Res*, 151, 403–8, (1986); and *Chem. Pharm*, 36, 784–90, (1988). Chitosan has additionally been reported as an effective immunomodulator in *Vaccine*, 4, 151–6, (1986); and K. Nishimura in *Chitin Derivatives in Life Sciences*, Ed., S. Tokura, Japan Chitin Soc., (1992).

Despite all of the research in the chitosan area, there is still a need for a practical application of chitosan that can benefit individuals on a daily basis, such as in the application to acute wounds obtained during a person's daily routine. Further, there is also a need for a wound healing system that takes advantage of the multiple medical benefits of chitosan in conjunction with other non-traditional wound healing chemistries.

While nicotinic acid (niacin), niacinamide (vitamin B3), ascorbic acid and niacinamide ascorbate are known as dietary supplements, for a variety of functions, it is not believed that such uses have been in conjunction with epidermal wound healing functions.

There is therefore a need for an improved bandage, which continues to provide absorbent capacity while compressed over a wound site. There is a further need for such an absorbent bandage/wound dressing, which allows for the release of wound healing agents while continuing to absorb exudates from the wound site. Further, there is a need of a bandage with an absorbent pad which is capable of retaining or locking up the fluid and which provides a moist environment for wound healing. Still further, there is a need for an adhesive bandage, which does not utilize traditional antibiotic treatment, but which does promote wound healing. Finally, there is a need for an adhesive bandage which promotes wound healing in multiple ways, but which does not utilize agents which may cause an allergic response in certain individuals, and does so at an affordable price point.

SUMMARY OF THE INVENTION

The present invention addresses some of the difficulties and problems discussed above by providing a non-occlusive bandage that is capable of on-going absorption and retention of fluid from a wound, even under compression, while at the same time releasing agents to the wound that are beneficial for promoting a healthy environment and which promote rapid healing.

In an alternative embodiment, a bandage of the type used on acute wounds, burn wounds or irritations includes a first layer for covering the wound site and an area around the wound site, the first layer including a top surface and bottom surface;

a second layer over the first layer bottom surface, for absorbing exudates from the wound site; the second layer including a poly(ethyleneoxide)-based compound and a chitosan-based compound, and wherein at least one wound healing antimicrobial agent is associated with the bandage in a position where said wound healing antimicrobial agent will come in contact with the wound site, and which is transferable from the bandage to the wound site, upon contact with the wound site. In an alternative embodiment a bandage of the type used on acute wounds, burn wounds and irritations includes a first layer for covering the wound site and an area around the wound site, with the first layer including a top surface and bottom surface a second layer over the first layer bottom surface, for absorbing exudates from the wound site; the second layer including a poly(ethylene oxide)-based compound and a chitosan-based compound. A third layer is situated over the second layer, the third layer being of a perforated nonstick film layer, and wherein, at least one wound healing antimicrobial agent is associated with the bandage in a position where the antimicrobial agent will come in contact with the wound site, and which is transferable from the bandage to the wound site, upon contact with the wound site. In an alternative embodiment the antimicrobial agent is niacinamide ascorbate. In still a further alternative embodiment, the antimicrobial agent is situated on the perforated nonstick film layer.

The present invention further provides a method of making such a bandage which includes the steps of coating an elastomeric base sheet with a suitable skin-friendly adhesive, affixing a layer of absorbent padding containing releasable hemostatic, wound healing and antimicrobial agents and optionally, overlaying the absorbent layer with a porous nonstick layer.

In another alternative of the method, the hemostatic and wound healing agents include a chitosan-based substance and niacinamide ascorbate.

These and other features and advantages of the present invention will become apparent after a review of the following detailed description of the disclosed embodiments and the appended claims.

BRIEF DESCRIPTION OF THE DRAWINGS

FIG. 1 is a perspective view of an adhesive bandage, which is generally available in the prior Art.

FIG. 2 is an exploded perspective view of an adhesive bandage in accordance with the invention.

DETAILED DESCRIPTION OF THE INVENTION

Figure 3:
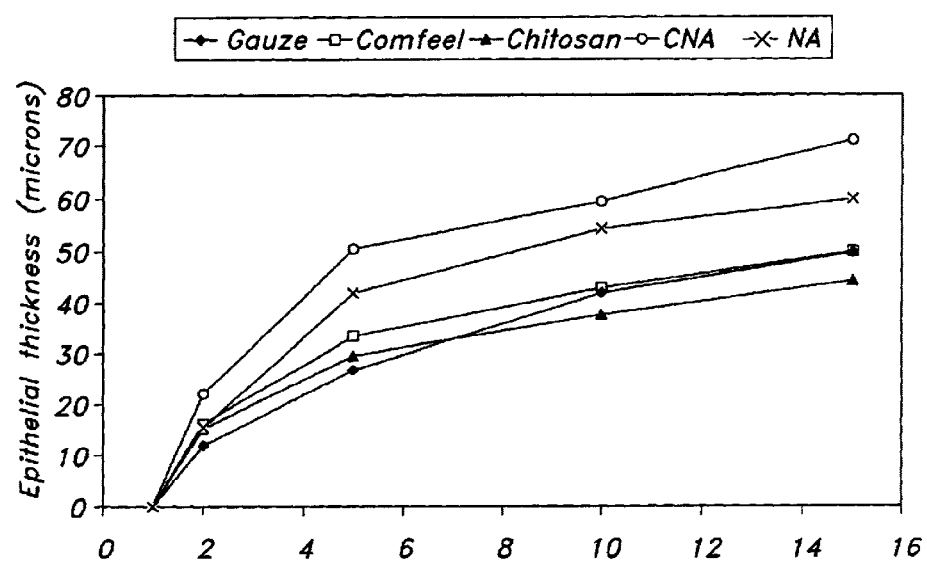
FIG. 3 is a graph illustrating a comparison of wound healing statistics in a rat model, for various substrates and test compounds over a period of 15 days.

Reference now will be made in detail to the embodiments of the invention, one or more examples of which are set forth below. Each example is provided by way of explanation and not limitation of the invention. It will be apparent to those of ordinary skill in the art that various modifications and variations can be made in the present invention without departing from the spirit and scope of the invention. It is intended that the present invention covers such modifications and variations as come within the scope of the appended claims and equivalents.

As used herein, the term 'bandage" shall be used interchangeably with "wound dressing" and "dressing", and shall refer to a covering to be placed over a wound.

As used herein, the term "transferable" shall be interchangeable with "releasable", and shall refer to the ability of a substance to be passed from a substrate such as a bandage, bandage layer or component, to a wound, through contact with the wound.

As used herein, the term "acute wound" shall refer to a wound caused by a traumatic abrasion, laceration or through superficial damage, and which is heals spontaneously without complications through normal phases of wound healing (such as hemostasis, inflammation, proliferation and remodeling).

As used herein, the tern "chronic wound" shall refer to a wound in which there is no clot formation, normally occurring in patients who are compromised in some fashion who are less likely to heal. When the body's natural healing process is delayed due to an underlying pathological process, such as a vascular insufficiency, it may lead to a chronic wound.

As used herein, the term "partial thickness wound" shall refer to a wound that is limited to the epidermis and superficial dermis with no damage to the dermal blood vessels.

As used herein, the term "full thickness wound" shall refer to a wound that involves total loss of epidermal and dermal layers of the skin, extending at least to the subcutaneous tissue layer and possibly as deep as the fascia-muscle layer and the bone.

As used herein, the term "nonwoven web" means a polymeric web having a structure of individual fibers or threads which are interlaid, but not in an identifiable, repeating manner. Nonwoven webs have been, in the past, formed by a variety of processes such as, for example, meltblowing processes, spunbonding processes, hydroentangling, air-laid and bonded carded web processes.

As used herein the term "spunbond" refers to small diameter fibers which are formed by extruding molten thermoplastic material as filaments from a plurality of fine, usually circular capillaries of a spinneret with the diameter of the extruded filaments being rapidly reduced as by for example in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,542,615 to Dobo et al.

As used herein the term "meltblown" means fibers formed by extruding a molten thermoplastic material through a plurality of fine, usually circular die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, in various patents and publications, including NRL Report 4364, "Manufacture of Super-Fine Organic Fibers" by B. A. Wendt, E. L. Boone and D. D. Fluharty; NRL Report 5265, "An Improved Device For The Formation of Super-Fine Thermoplastic Fibers" by K. D. Lawrence, R. T. Lukas, J. A. Young; and U.S. Pat. No. 3,849,241, issued Nov. 19, 1974, to Butin, et al.

As used herein the term "sheet material" refers to nonwoven webs, polymeric films, polymeric scrim-like materials, and polymeric foam sheeting. The term film shall include breathable and non-breathable monolithic film, porous, and non-porous film, and apertured and non-apertured film.

As used herein the term "laminate" refers to a composite structure of two or more sheet material layers that have been adhered through a bonding step, such as through adhesive bonding, thermal bonding, point bonding, pressure bonding or ultrasonic bonding.

As used herein the terms "elastic" and "elastomeric" refers to sheet material which, upon application of a biasing force, is extensible or elongatable in at least one direction.

As used herein, the term "inelastic" or "nonelastic" refers to any material which does not fall within the definition of "elastic" above.

As used herein, the term "coform" means a process in which at least one meltblown diehead is arranged near a chute through which other materials are added to the web while it is forming. Such other materials may be pulp, superabsorbent particles, cellulose or staple fibers, for example. Coform processes are shown in commonly assigned U.S. Pat. No. 4,818,464 to Lau and U.S. Pat. No. 4,100,324 to Anderson et al. each incorporated by reference in their entirety.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 4,795,668 to Krueger et al., and U.S. Pat. No. 5,336,552 to Strack et al. Conjugate fibers are also taught in U.S. Pat. No. 5,382,400 to Pike et al., and may be used to produce crimp in the fibers by using the differential rates of expansion and contraction of the two or more polymers. For two component fibers, the polymers may be present in varying desired ratios. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

The present invention includes a grafted polyethyleneoxide PEO that, upon exposure to moisture, crosslinks into a gel structure capable of absorbing relatively large amounts of fluids, such as water or saline. Such grafted PEO may be used on or in a bandage, as a coating, film, fibrous material or foam material. Such material is used in combination with a hemostatic agent and an antimicrobial/wound healing agent, in either the same layer or in separate layers.

In accordance with the present invention, PEO is graft polymerized with an organic moiety capable of graft polymerization with PEO which moiety contains a trialkoxy silane functional group or which moiety reacts with water to form a silanol group. The silane graft modified PEO resin can be thermally processed into functional forms, such as films, fibers and foams. When these functional forms are exposed to moisture, a crosslinking reaction occurs, by the mechanism shown below, to provide a gel structure capable of absorbing relatively large amounts of water, such as more than 20 grams of saline per gram of polymer under free swell conditions, making such materials ideal for an absorbent pad within a bandage. Water-soluble polymers useful in the present invention include, but are not limited to, poly (alkylene oxides), such as poly(ethylene oxide) ("PEO"), poly(ethylene glycols), block copolymers of ethylene oxide and propylene oxide, poly(vinyl alcohol) and poly(alkyl vinyl ethers). These water-soluble polymers must be capable of graft polymerization with an organic moiety containing a trialkoxy silane functional group or a moiety that reacts with water to form a silanol group. The preferred water-soluble polymer for use in the present invention is PEO. The process for the graft polymerization of PEO with methacryloxypropyl trialkoxy silane followed by cross-linking upon exposure to moisture is shown below.

Graft Polymerization of PEO with Methacryloxypropyl Trialkoxy Silane followed by Exposure to Moisture

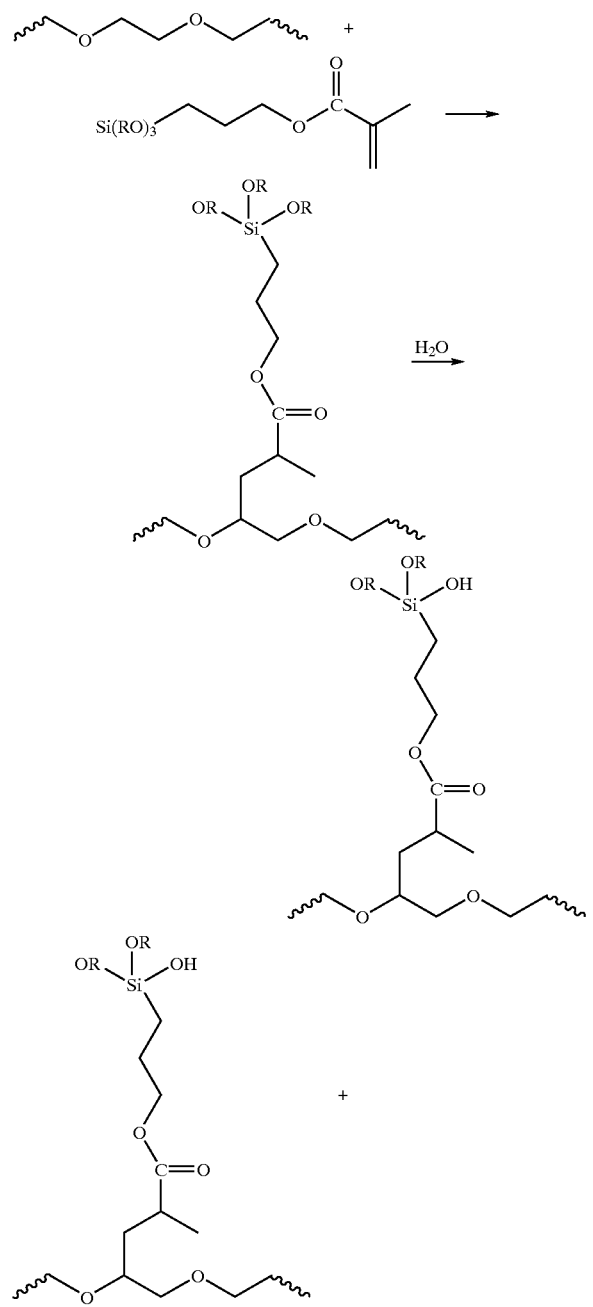

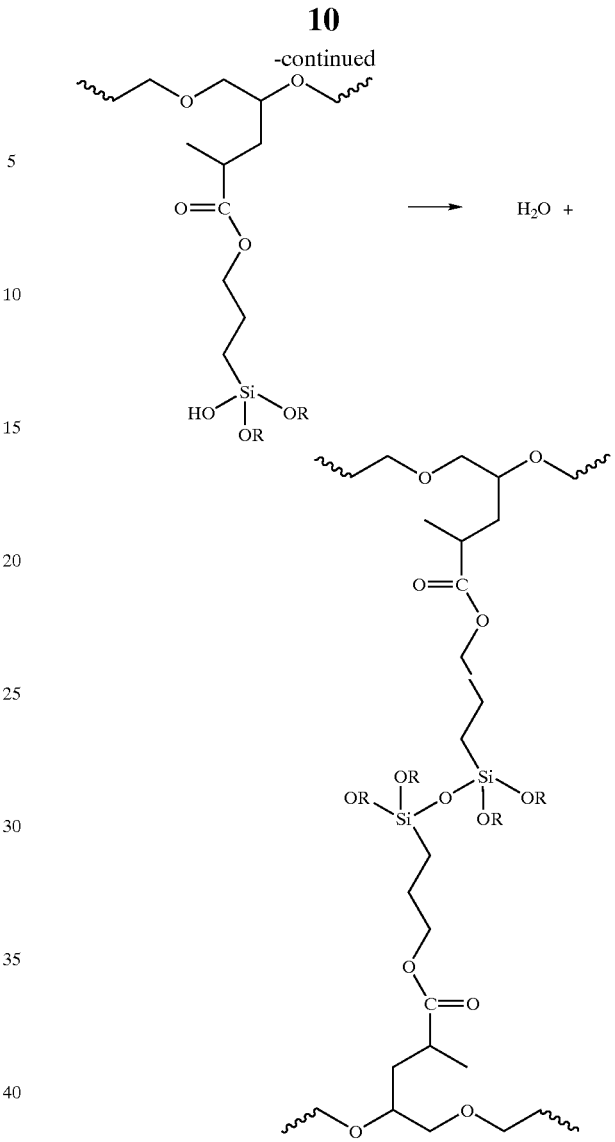

Since crosslinking of the silane graft modified PEO does not normally occur during thermal processing, the graft modified PEO of the present invention provides for more robust thermal processing into functional forms. Furthermore, since the process of forming the silane graft modified PEO of the present invention does not require the use of aqueous solutions, there are no costly and time consuming evaporation steps involved.

The PEO resins useful for graft modification in accordance with the present invention include, but are not limited to, PEO resins having initial reported approximate molecular weights ranging from about 10,000 g/mol to about 8,000,000 g/mol as determined by rheological measurements. All molecular weights are given on a weight average basis unless otherwise indicated.

Such PEO resins are commercially available from, for example, Union Carbide Corporation having offices in Danbury, Conn., and are sold under the trade designations POLYOX® 205, POLYOX® N-10, POLYOX® N-80, POLYOX® WSR N-750, POLYOX® WSR N-12K and POLYOX® UCARFLOC® Polymer 309.

Fibers, films and foams can be made using conventional processing methods from commercially available PEO resins when modified in accordance with this invention. The PEO resins useful for modification for fiber-making purposes include, but are not limited to, PEO resins having initial reported approximate molecular weights ranging from about 50,000 g/mol to about 400,000 g/mol. Higher molecular weights are desired for increased mechanical and physical properties and lower molecular weights are desired for ease of processing. Desirable PEO resins for fiber making have molecular weights ranging from 50,000 to 300,000 g/mol before modification and more desired PEO resins for fiber making have molecular weights ranging from 50,000 to 200,000 g/mol before modification. The PEO compositions modified from PEO resins within the above resins provide desirable balances between mechanical and physical properties and processing properties. Three PEO resins within the above preferred ranges are commercially available from Union Carbide Corporation and are sold under the trade designations POLYOX® N-750, POLYOX® WSR N-10 and POLYOX® WSR N-80. These three resins have reported approximate molecular weights, as determined by rheological measurements, of about 100,000 g/mol to 300,000 g/mol.

Other PEO resins available from, for example, Union Carbide Corporation, within the above approximate molecular weight ranges are sold under the trade designations WSR N-750, WSR N-3000, WSR-3333, WSR-205, WSR-N-12K, WSR-N-60K, WSR-301, WSR Coagulant, WSR-303. (See POLYOX®: Water Soluble Resins, Union Carbide Chemicals & Plastic Company, Inc., 1991 which is incorporated by reference herein in its entirety.) Both PEO powder and pellets of PEO can be used in this invention since the physical form of PEO does not affect its behavior in the melt state for grafting reactions. This invention has been demonstrated by the use of PEO in powder form as supplied by Union Carbide. However, the PEO resins to be modified may be obtained from other suppliers and in other forms, such as pellets. The PEO resins and modified compositions may optionally contain various additives, such as, plasticizers, processing aids, rheology modifiers, antioxidants, UV light stabilizers, pigments, colorants, slip additives, antiblock agents, etc., which may be added before or after modification.

Organic monomers capable of graft polymerization with PEO which monomers contain a trialkoxy silane functional group or a moiety that reacts with water to form a silanol group are useful in the practice of this invention. The trialkoxy silane functional group has the following structure:

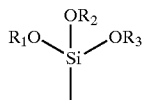

wherein $R_1$, $R_2$ and $R_3$ are alkyl groups independently having from 1 to 6 carbon atoms. The term "monomer(s)" as used herein includes monomers, oligomers, polymers, mixtures of monomers, oligomers and/or polymers, and any other reactive chemical species which is capable of covalent bonding with the parent polymer, PEO. Ethylenically unsaturated monomers containing a trialkoxy silane functional group are appropriate for this invention and are desired. Desired ethylenically unsaturated monomers include acrylates and methacrylates. A particularly desirable ethylenically unsaturated monomer containing a trialkoxy silane functional group is methacryloxypropyl trimethoxy silane. Methacryloxypropyl trimethoxy silane is commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, provide the desired effects to PEO and are effective monomers for grafting in accordance with the present invention.

The amount of organic monomer having trialkoxy silane functional groups or silanol-forming functional groups relative to the amount of PEO may range from about 0.1 to about 20 weight percent of monomer to the weight of PEO. Desirably, the amount of monomer should exceed 0.1 weight percent in order sufficiently to improve the processability of the PEO. A range of grafting levels is demonstrated in the Examples. Typically, the monomer addition levels are between about 1.0% and about 15% of the weight of the base PEO resin; particularly, between about 1.0% and about 10% of the weight of the base PEO resin; especially, between about 1.5% and about 5.5% of the weight of the base PEO resin for some intended uses. Desirably, for uses involving bandage applications, the grafting level is in the range of 0.5 to about 10 weight percent relative to the weight of the PEO.

A variety of initiators may be useful in the practice of this invention. When grafting is achieved by the application of heat, as in a reactive-extrusion process, it is desirable that the initiator generates free radicals through the application of heat. Such initiators are generally referred to as thermal initiators. For the initiator to function as a useful source of radicals for grafting, the initiator should be commercially and readily available, stable at ambient or refrigerated conditions, and generate radicals at reactive-extrusion temperatures.

Compounds containing an O—O, S—S, or N=N bond may be used as thermal initiators. Compounds containing O—O bonds; i.e., peroxides, are commonly used as initiators for graft polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t-butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile abbreviated as AIBN, 2,2'-azobis(2,4-dimethylpentanenitrile) and 1,1'-azobis (cyclohexanecarbonitrile) may be used as the initiator. This invention has been demonstrated in the following Examples by the use of a liquid, organic peroxide initiator available from R.T. Vanderbilt Company, Inc. of Norwalk, Conn., sold under the trade designation VAROX DBPH peroxide which is a free radical initiator and comprises 2,5-bis(tert butylperoxy)-2,5-dimethyl hexane along with smaller amounts of di(tert butylperoxide). Other initiators may also be used, such as LUPERSOL® 101 and LUPERSOL® 130 available from Elf Atochem North America, Inc. of Philadelphia, Pa.

A variety of reaction vessels may be useful in the practice of this invention. The modification of the PEO can be performed in any vessel as long as the necessary mixing of PEO, the monomer and the initiator is achieved and enough thermal energy is provided to affect grafting. Desirably, such vessels include any suitable mixing device, such as Brabender Plasticorders, Haake extruders, Bandbury mixers, single or multiple screw extruders, or any other mechanical mixing devices which can be used to mix, compound, process or fabricate polymers. In a desired embodiment, the reaction device is a counter-rotating twin-screw extruder, such as a Haake extruder available from Haake, 53 West Century Road, Paramus, N.J. 07652 or a co-rotating, twin-screw extruder, such as a ZSK-30 twin-screw, compounding extruder manufactured by Werner & Pfleiderer Corporation of Ramsey, N.J. It should be noted that a variety of extruders may be used to modify the PEO in accordance with the invention provided that mixing and heating occur.

The present invention is further illustrated by the following preliminary examples which focus initially on the formation of such PEO material and its uses as films, fibers, and coatings. The examples are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

General Procedures

In the examples all percentages are given on a weight basis unless otherwise indicated.

All molecular weights are given on a weight average basis unless otherwise indicated.

Water absorbency under unrestrained conditions (free swell) of copolymers that can be used in the subject coatings was tested according to the following method (unless otherwise stated). A sample of film or resin pellet with a weight of 30 to 50 milligrams is weighed in the dry state to the nearest tenth of a milligram. The test sample is place in a 500 ml bottle to which 100 ml of distilled water is added. The bottle is shaken on a laboratory shaker for 30 minutes at room temperature. The contents of the bottle are filtered under vacuum with a Beuchner funnel using Whatman 55 mm filter paper. The swollen sample is removed from the filter paper and weighed to the nearest milligram. Gram per gram uptake is calculated as the wet weight of recovered (insoluble) material, divided by the initial dry weight of the sample, minus 1. Generally, the average of 5 replicates is reported. A similar procedure is used with 0.9% saline replacing distilled water.

Uptake of simulated menses or saline solution was determined for the coatings as follows: Samples of the copolymer to be tested were weighed and then soaked in 20 ml of saline or menses simulant composed of swine blood of controlled hematocrit with albumin added to simulate the visco-elastic properties of menses. The samples were soaked for 30 minutes, removed, the excess fluid was drained from the surface, and the wet samples were then weighed. This weight is used to calculate the saturated uptake. The sample is then placed under a pressure of 0.5 psi and then weighed again to determine the blotted uptake after expressed fluid has drained from the sample. The amount of fluid that remains in the sample is used to calculate the fluid uptake at 0.5 psi.

EXAMPLE 1

This example illustrates the synthesis of a graft copolymer from poly(ethylene oxide) engrafted with 3-(trimethoxysilyl) propyl methacrylate that is useful in the coatings of the present invention.

Polyethylene oxide ("PEO"), supplied by Union Carbide under the name POLYOX Water Soluble Resins, was used. POLYOX WSR-205 having a molecular weight of about 600,000 g/mol was used in powder form. The reactive polar vinyl monomer used was 3-(trimethoxysilyl) propyl methacrylate supplied by Aldrich Chemical Company and manufactured by Dow Corning under the trade name, Dow Corning Z-6030 Silane. The peroxide initiator used was Varox DBPH, supplied by R. T. Vanderbilt Company, Inc.

The monomer is composed of two functional groups. The methacrylate function reacts with PEO after a free radical site is initiated with peroxide. The resultant modified PEO resin is still thermally processable as long as it is kept relatively dry. The crosslinking takes place from the other end of the molecule at the alkoxysilane function. The alkoxysilane is readily hydrolyzed into a more reactive silanol and the silanol condenses with another silanol to form a cross-linked network. Because the grafting monomer has three alkoxysilanes, each graft site is theoretically capable of forming three crosslinks. Use of this type of grafting monomer provides a modified resin, which, while kept relatively dry, can be fabricated into useful structures, and then, when exposed to humid air, become crosslinked. The result is a material that retains the versatility of thermal processability into a variety of structures along with the capability of using those structures for absorbency. This unusual combination of features is available because the crosslinked, hydrophilic network is generated after the structure is fabricated.

A bench-scale HAAKE twin-screw extruder was used. This unit contains a set of custom-made, counter-rotating conical twin screws. Screw Design for the HAAKE Extruder:

A general characteristic description is provided in Table 1 since the exact dimensions may be proprietary to the extruder manufacturer.

TABLE 1

Extruder characteristics.

| SECTIONS | DESCRIPTIONS |
| --- | --- |
| Section 1: | A double flighted forward pumping section: Large screw lead (pitch) and a high helix angle |
| Section 2: | A double flighted forward pumping section: Screw pitch is smaller than Section 1 |
| Section 3: | A double flighted forward pumping section: Screw pitch is smaller than Section 2 |
| Section 4: | A double flighted and notched reversed pumping section One complete flight with notches |
| Section 5: | A double flighted notched forward pumping section Two complete flights |
| Section 6: | A double flighted forward pumping section Screw pitch is between sections 1 and 2. |

The die has two openings of 3 mm in diameter, which are separated by 10 mm. The strands were cooled in air and subsequently pelletized. The feed section was not heated, rather it was cooled by water. The extruder has three heating sections from the feeding section towards the die designated as Zone 1, Zone 2, and Zone 3. The die was designated as Zone 4.

The first reactive extrusion was done on a HAAKE twin screw extruder of 10/1 L/D with custom designed screws (described above) at a rate of 5 pounds per hour. The pelletized POLYOX 205 was metered into the throat of the extruder at a rate of 37.8 g/min with a K-Tron feeder. In the same manner, Varox DBPH peroxide was metered at a rate equivalent to 0.25 weight percent of the POLYOX 205 and the Z-6030 silane was metered in with an Eldex pump at a rate of 2 to 5 weight percent of the POLYOX 205. The temperature profile for the heating zones were 150°, 160°, 160°, and 170° C. The screw speed was 150 rpm. The strands were cooled in air using a fan-cooled conveyer belt. The solidified strands of the grafted POLYOX 205 were then pelletized using a Conair pelletizer.

The sample pellets from this experiment were stored under ambient conditions for four months and then under high humidity (33° C. and 80% relative humidity) for seven days. The resin samples were tested to determine the ultimate gel fraction according to the procedure described below. The gel fraction is the portion of the sample that is cross-linked and no longer soluble in water. The soluble fraction is equal to 1-(gel fraction).

Gel Fraction Test:

A sample of film or resin pellet with a weight of 30 to 50 milligrams is weighed in the dry state to the nearest tenth of a milligram. The test sample is place in a 500 ml bottle to which 100 ml of distilled water is added. The bottle is shaken on a laboratory shaker for 30 minutes at room temperature. The contents of the bottle are filtered under vacuum with a Beuchner funnel using Whatman 55 mm filter paper (catalogue # 1001 55) which was pre-dried at 60° C. and weighed to the nearest tenth of a milligram. The insoluble portion of the sample is dried along with the filter paper at 60° C. for two hours and then weighed to determine the dry weight of insoluble material.

Gel fraction or percent gel is taken as the dry weight of recovered (insoluble) material divided by the initial dry weight of the sample. Generally, the average of 5 replicates is reported in Table 2 below:

TABLE 2

Gel fraction in several samples of graft copolymer

| SAMPLE | WEIGHT PERCENT Z6030 | WEIGHT PERCENT VAROX DBPH | EXTRUDER PRESSURE (PSI) | GEL FRACTION |
|---|---|---|---|---|
| 1-1 | 0 | 0 | 530 | 0 |
| 1-2 | 2 | 0.15 | 330 | 0.91 |
| 1-3 | 5 | 0.25 | 430 | Not tested |

The addition of the monomer and peroxide initiator results in a reduction in extruder pressure compared to the control. The reduced pressure is indicative of reduced melt viscosity. This result indicates that the PEO has been modified into a form that is water-absorbent and not completely water-soluble like the control resin (sample 1—1).

EXAMPLE 2

The following samples were prepared using the same method and extruder temperatures as described above in Example 1 and using the proportions of ingredients indicated in Table 3 below. Since the first sample resulted in low extruder pressure, the temperatures were reduced to bring the extruder pressure into the proper range.

TABLE 3

Production parameters for extrusion/reaction.

| SAMPLE | WEIGHT % VINYL TRI-ETHOXY SILANE | WEIGHT % VAROX DBPH | EXTRUDER PRESSURE (PSI) | COMMENTS, OBSERVATIONS |
|---|---|---|---|---|
| 2-1-a | 5 | .25 | 92 | Very low pressure, temperatures reduced to 120, 130, 130, 140 |
| 2-1-b | 5 | .25 | 270 | Low melt viscosity |
| 2-2 | 2 | .15 | 350 | Slight pressure increase |
| 2-3 | 0 | 0 | 700 | P205 control, high pressure, rough strands |

Pellets from samples 2-1-b, 2—2 and 2-3 were stored for approximately ten weeks under laboratory conditions, exposed to ambient humidity. All three samples aged under these conditions, dissolved in water after standing overnight.

The resin samples prepared with triethoxy vinyl silane remained water-soluble. This result suggests that this monomer was not grafted onto P205 under the same conditions that were effective for grafting Z6030. The significant reduction in melt pressure and melt viscosity indicates that chain scission of the PEO was occurring rather than grafting. Different conditions or initiators may be needed to induce grafting between PEO and triethoxy vinyl silane.

EXAMPLE 3

A third reactive extrusion experiment was conducted to evaluate the effect of higher addition level of the Z6030 monomer along with proportionately higher addition of the peroxide initiator. The same screw design and production rate as Example 1 was used. The pelletized POLYOX 205 was metered into the throat of the extruder at a rate of 37.8 g/minute with a K-Tron feeder. Dow Corning Z-6030 Silane was metered into the throat of the extruder with an Eldex pump at a rate of 3.78 g/minute, equivalent to ten weight percent of the POLYOX 205. In the same manner, Varox DBPH peroxide was metered at a rate equivalent to 0.40 weight percent of the POLYOX 205. A second code was run at five weight percent addition of Z6030 with Varox DBPH peroxide metered at a rate equivalent to 0.33 weight percent of the POLYOX 205. The temperature profile for the heating zones were 150°, 160°, 160°, and 170° C. The strands were cooled in air using a fan-cooler conveyor belt. The solidified strands of the grafted POLYOX 205 were then pelletized on a Conair pelletizer.

The sample descriptions and gel fraction results are shown in the Table 4 below. These gel fraction results were obtained after six months at ambient conditions followed by one week at 80% relative humidity.

TABLE 4

*Gel fractions generated in samples of a graft copolymer.*

| SAMPLE | WEIGHT % Z6030 | WEIGHT % VAROX DBPH | EXTRUDER PRESSURE (PSI) | GEL FRACTION |
|---|---|---|---|---|
| 3-1 | 10 | .40 | 420 | .92 |
| 3-2 | 5 | .33 | 450 | .95 |

These result indicate that five percent Z6030 is sufficient monomer to provide a nearly fully crosslinked, PEO gel.

EXAMPLE 4

The Z6030 reactive grafting was done with a ZSK-30 extruder. A ZSK-30 co-rotating, twin-screw extruder (manufactured by Werner & Pfleiderer) with 14 barrel sections and 1338 mm total processing section length was used. The first barrel was not heated, but cooled by water. The peroxide was injected into barrel #5 and the Z6030 monomer was injected into barrel #6. Both chemicals were injected via a pressurized nozzle injector. The die has four openings of 3 mm in diameter, which are separated by 7 mm. Polymer strands were extruded onto an air-cooling belt and subsequently pelletized.

The following extruder barrel temperatures (in ° C.) were set to the following levels during the extrusion as shown in Table 5:

TABLE 5

*Extruder conditions during reactive grafting.*

| ZONE 1 | ZONE 2 | ZONE 3 | ZONE 4 | ZONE 5 |
|---|---|---|---|---|
| 166° | 180° | 180° | 180° | 180° |

The polymer melt temperature was 195°–205° C. The polymer strands were cooled on a stainless steel cooling belt and subsequently pelletized.

TABLE 6

*ZSK-30 Screw Configuration for Reactive Extrusion*

| ELEMENT NO. | DESCRIPTION | ELEMENT NO. | DESCRIPTION |
|---|---|---|---|
| 1 | PKR 10 | 31 | KB45/5/14 |
| 2 | 20/10 | 32 | KB45/5/14 |
| 3 | 42/42 | 33 | 20/20 |
| 4 | 42/42 | 34 | 20/20 |
| 5 | 28/28 | 35 | 20/20 |
| 6 | 28/28 | 36 | 28/28 |
| 7 | 20/20 | 37 | 28/28 |
| 8 | 20/20 | 38 | 28/28 |
| 9 | KB45/5/28 | 39 | 20/20 |
| 10 | KB45/5/14 | 40 | 20/10 LH |
| 11 | 28/28 | 41 | 42/42 SK |
| 12 | 28/28 | 42 | 42/42 SK |
| 13 | 28/28 | 43 | 42/42 |
| 14 | 28/28 | 44 | 20/20 |
| 15 | 20/20 | 45 | 20/20 |
| 16 | 28/28 | 46 | 20/20 |
| 17 | 28/28 | 47 | 20/20 |
| 18 | 20/20 | 48 | 20/20 |
| 19 | KB45/5/42 | 49 | 20/20 |
| 20 | 28/28 | 50 | 20/20 |
| 21 | 20/20 | 51 | 20/20 |
| 22 | KB45/5/28 | 52 | 20/20 |
| 23 | KB45/5/14 LH | 53 | 20/10 |
| 24 | 28/28 | 54 | 20/10 |
| 25 | 20/20 | 55 | 20/10 |
| 26 | 20/20 | 56 | 20/10 |
| 27 | 28/28 | 57 | 20/10 |
| 28 | 28/28 | 58 | 20/10 |
| 29 | 20/20 | 59 | 20/10 |
| 30 | 20/20 | 60 | 14/14 |

The PEO powder resin was fed into the ZSK-30 extruder with a K-Tron volumetric feeder at a throughput of 20 lbs/hr. The modified PEO strands were cooled between stainless steel belts that were cooled with water from the opposite side followed by pelletization. The results are shown in Table 7 below:

TABLE 7

*Gel characteristics as a function of grafting variables.*

| SAMPLE | WEIGHT % Z6030 | WEIGHT % VAROX DBPH | EXTRUDER PRESSURE (PSI)/% TORQUE/MELT TEMPERATURE ° C. | GEL FRACTION |
|---|---|---|---|---|
| 4-1 | 5.6 | .165 | 320/46%/214 | 0.94 |
| 4-2 | 5.6 | .33 | 320/46%/216 | Not tested |
| 4-3 | 11.3 | .33 | 380/47%/218 | Not tested |
| 4-4 | 11.3 | .66 | 390/48%/216 | 0.96 |

The variation in monomer and peroxide levels had minimal effect on the process data for pressure and torque. Gel fraction for samples 4-1 and 4-4 was tested after four months at ambient temperature and humidity and one week at elevated humidity and temperature (33° C. and 89% relative humidity).

EXAMPLE 5

Another reactive extrusion run on the ZSK-30 was designed to determine the effect of peroxide initiator addition and screw rpm, which determines residence time for the reaction, upon the resin properties. The silane monomer addition level was held constant at 1.3 mole percent (based on moles of ethylene oxide repeat) or 7.3 weight percent. The standard settings for temperature were the same as described in Example 4.

The settings for the experimental variables and the process data collected during the experiment are shown in Table 8, below.

TABLE 8

*Variable Settings and Process Data*

| Run # | VARIABLE Rpm | SETTINGS Wt. % Peroxide | PROCESS Melt Temp (° C.) | RESPONSE Percent of maximum Torque | DATA Melt Pressure |
|---|---|---|---|---|---|
| 5-1 | 300 | 0.22 | 210 | 45 | 600 |
| 5-2 | 100 | 0.22 | 200 | 85 | 810 |

TABLE 8-continued

Variable Settings and Process Data

| Run # | VARIABLE Rpm | SETTINGS Wt. % Peroxide | PROCESS Melt Temp (° C.) | RESPONSE Percent of maximum Torque | DATA Melt Pressure |
|---|---|---|---|---|---|
| 5-3 | 100 | 0.13 | 200 | 86 | 830 |
| 5-4 | 300 | 0.13 | 205 | 42 | 700 |
| 5-5 | 200 | 0.17 | 205 | 50 | 800 |
| 5-6 | 100 | 0.13 | 201 | 86 | 890 |
| 5-7 | 300 | 0.13 | 206 | 43 | 700 |
| 5-8 | 300 | 0.22 | 206 | 42 | 600 |
| 5-9 | 100 | 0.22 | 199 | 85 | 780 |

The process data in Table 8 indicates a significant effect of the screw rpm upon the torque. Note that a reduction in rpm from 300 to 100 results in the torque readings increasing to nearly double. A significant, but less dramatic increase is observed in the melt pressure at the reduced rpm setting. Changes in the peroxide addition level had minimal effect on torque or pressure within the range studied.

Gel fraction results 165 hours cure at 33° C. and 80% relative humidity are shown in Table 9 below:

TABLE 9

Gel fraction results for several resins.

| RESIN SAMPLE | RPM | WEIGHT % VAROX DBPH | GEL FRACTION |
|---|---|---|---|
| 5-6 | 100 | 0.13 | 0.87 |
| 5-7 | 300 | 0.13 | 0.82 |
| 5-8 | 300 | 0.22 | 0.84 |
| 5-9 | 100 | 0.22 | 0.85 |

EXAMPLE 6

To provide a modified PEO resin suitable for fiber spinning, a lower molecular weight PEO, POLYOX N-80, was used as the starting resin for reactive grafting on the ZSK-30 extruder. The initial molecular weight of this resin was 200,000 g/mol. Temperature settings for the extruder were the same as Examples 4 and 5. Other process settings are shown in the Table 10 below.

TABLE 10

Process settings for extruder reactive/grafting.

| RESIN SAMPLE | WT % Z6030 | WT % VAROX DBPH | RPM | PROCESS DATA PRESSURE/ TORQUE | GEL FRACTION |
|---|---|---|---|---|---|
| 6-1 | .3 | 0.17 | 200 | 190/59 | 0.62 |

The lower molecular weight PEO results in lower extruder pressure compared to the POLYOX 205.

In the examples that follow, the modified PEO resin was converted into film within one or two days of preparation so that the resin would still be in an uncrosslinked state.

For film processing, a Haake counter-rotating, twin-screw extruder was used with a 4 inch slit die attached. A chilled wind-up roll maintained at 15°–20° C. was used to collect the film. The temperature profile for the four heating zones was 170°, 180°, 180° and 190° C. Screw speed and wind-up speed were adjusted such that the film thickness was 2 to 3 mil. The process was allowed to stabilize before the film was collected. Film samples were tested for gel fraction according to the test method previously described. In addition, the films were tested for fluid absorbency (gram per gram uptake) under unrestrained swelling conditions according to the following test method.

Gram per Gram Uptake (Free Swell)

A sample of film or resin pellet with a weight of 30 to 50 milligrams is weighed in the dry state to the nearest tenth of a milligram. The test sample is place in a 500 ml bottle to which 100 ml of distilled water is added. The bottle is shaken on a laboratory shaker for 30 minutes at room temperature. The contents of the bottle are filtered under vacuum with a Beuchner funnel using Whatman 55 mm filter paper. The swollen sample is removed from the filter paper and weighed to the nearest milligram.

Gram per gram uptake is calculated as the wet weight of recovered (insoluble) material, divided by the initial dry weight of the sample, minus 1. Generally, the average of 5 replicates is reported. A similar procedure is used with 0.9% saline replacing distilled water.

Films from Examples 1 and 2 were conditioned in a high humidity environment (80% relative humidity at 33° C.) for 16 hours. Four film samples were cut and weighed: 5% silane (dry film), 5% silane (humidity conditioned), 2% silane (dry film), 2% silane (humidity conditioned). The films were place in a vial of 20 ml of 0.9% saline and kept at 35 C. After 16 hours in a free swell condition, the liquid was poured off and the gel isolated, blotted to remove surface moisture, and weighed. Gram per gram uptake under these conditions is shown in Table 11 below.

TABLE 11

| FILM SAMPLE | RESIN SOURCE | DE- SCRIPTION | AMBIENT CONDITION UPTAKE | HUMIDIFIED CONDITION UPTAKE |
|---|---|---|---|---|
| 7-2 | 1-2 | 2% Z6030 | 3 g/g | 9 g/g |
| 7-3 | 1-3 | 5% Z6030 | 23 g/g | 20 g/g |
| 7-4 | 2-1-b | 5% vinyl silane | Dissolved | Dissolved |
| 7-5 | 2-2 | 2% vinyl silane | Dissolved | Dissolved |

These initial results indicate the high absorbency of modified PEO resins when they are successfully grafted and allowed to crosslink. However, if grafting is not successful, as in samples 7-4 and 7-5, the film responds to saline much like unmodified PEO and dissolves.

Uptake of Simulated Menses

Since PEO crosslinked by other means was previously known to be an effective absorbent for menses, films from this extrusion experiment were also tested for absorbency with simulated menses.

Films samples (1.5"×1.5"), prepared from POLYOX 205 grafted with five percent Z6030, were soaked in 20 ml of menses simulant composed of swine blood of controlled hematocrit with albumin added to simulate the visco-elastic properties of menses. The samples were soaked for 30 minutes, removed, the excess fluid was drained from the surface, and then weighed. This weight is used to calculate the saturated uptake. The sample is then placed under pressure of 0.5 psi and then weighed again to determine the blotted uptake. The results are shown below in Table 12:

TABLE 12

| SAMPLE | SATURATED UPTAKE (G/G) | BLOTTED UPTAKE (G/G) |
|---|---|---|
| 5% Z6030, ambient (for 2 months) | 21 | 10 |
| 5% Z6030, humidified 24 hr. | 13 | 10 |

Thermal Analysis

Table 13 below contains the differential scanning calorimeter ("DSC") results for the Z6030 grafted POLYOX 205 in comparison to the ungrafted resin. Both the heating and the cooling rates were 20° C. per minute. There are several notable differences in the grafted polymer compared to the ungrafted P205.

1. There is a significant increase in the crystallization temperature (Tc) for the grafted resins. (~40° C. for the ungrafted resin compared to ~47° C. for the grafted).
2. Based on the second heat cycle (which erases prior heat history effects) the grafted resins appear to have a lower melt temperature and a slightly higher glass transition temperature ($T_g$) compared to the unmodified resin.

TABLE 13

Initial Thermal Analysis Results

| | POLYOX 205 (UNMODIFIED) | 2% Z6030 | HUMIDIFIED CONDITION | 5% Z6030 | HUMIDIFIED CONDITION |
|---|---|---|---|---|---|
| Film resin source | 1-1 | 1-2 | 1-2 | 1-3 | 1-3 |
| $1^{st}$ heat Tg (C) | −55.7 | −52.2 | −54 | −55.5 | −54.5 |
| Tm (onset/peak) | 60.4/71.3 | 56.8/62.6 | 60.6/67.2 | 56/61.7 | 58.7/66.1 |
| heat of fusion | 126 | 124 | 166 | 139 | 162 |
| estimated crystallinity (100% = 213 J/g) | 59% | 58% | 78% | 65% | 76% |
| Tc (onset/peak) | 47/39.8 | 49.3/46 | 50/47.9 | 49.4/47 | 50/48.7 |
| heat of fusion | 114 | 116 | 134 | 130 | 126 |
| estimated crystallinity (100% = 213) | 54% | 54% | 63% | 61% | 59% |
| 2nd heat Tg | −55.6 | −46 | | −50.5 | |
| 2nd heat Tm (onset/peak) | 60.5/71.3 | 59.2/64.7 | 58.6/64.4 | 58.1/63.9 | 57.9/63.4 |
| heat of fusion | 122 | 122 | 139 | 136 | 140 |
| estimated crystallinity (100% = 213) | 57% | 57% | 65% | 64% | 66% |

Film Properties

Film properties for the Z6030 grafted POLYOX 205 are shown in Table 14 below for both ambient conditions and humidified film. For the sake of comparison, the properties of POLYOX 205 grafted with hydroxyethyl methacrylate ("HEMA") are also shown. In general, the ambient films have similar properties to the HEMA grafted film, particularly low modulus, high break stress, and high elongation at break. The most notable change for films that have been conditioned under high humidity to induce crosslinking is an increase in the film modulus.

TABLE 14

Film Properties from Initial Extrusion Experiment

| FILM RESIN SOURCE | FILM ORIENTATION | THICKNESS (MILS) | BREAK STRESS (MPA) | % STRAIN @ BREAK | MODULUS (MPA) | ENERGY TO BREAK (J/CC) |
|---|---|---|---|---|---|---|
| 1-3 | MD | 3.18 | 22.2 | 1075 | 103 | 159 |
| 1-3 | CD | 3.13 | 23.4 | 1132 | 146 | 179 |
| 1-2 | MD | 2.98 | 14.2 | 843 | 162 | 105 |
| 1-2 | CD | 2.96 | 13.7 | 592 | 226 | 75 |
| 205 grafted with 1.5% HEMA | MD | 1.16 | 25.4 | 1153 | 163 | 174 |

Note that films 1–3 have not been conditioned, in that they have been prepared at ambient conditions. Films 1–2 have been conditioned under high humidity.

result from the formation of crosslinks under the curing condition are evident. For this table, the cure condition was 92 hours at 37° C. and 80% relative humidity.

TABLE 15

Film Properties as a Function of Cure

| Sample MD Film Properties | Break stress (Mpa) | | % Strain @ break | | Modulus (Mpa) | | Energy to Break (J/cc) | |
|---|---|---|---|---|---|---|---|---|
| | Uncross-linked | cross-linked | Uncross-linked | cross-linked | Uncross-linked | cross-linked | Uncross-linked | cross-linked |
| Film 8-1 (Resin 4-1): 5.6% Z6030 .16% peroxide | 21.8 | 30.6 | 942 | 1127 | 143 | 192 | 136 | 213 |
| Film 8-2 (Resin 4-2): 5.6% Z6030 .33% peroxide | 20.9 | 25.9 | 1158 | 1084 | 132 | 177 | 156 | 177 |
| Film 8-3 (Resin 4-3): 11.2% Z6030 .33% peroxide | 19.5 | 27.7 | 1034 | 1105 | 111 | 173 | 132 | 188 |
| Film 8-4 (Resin 4-4): 11.2% Z6030 .66% peroxide | 19.8 | 25.3 | 1052 | 1008 | 133 | 190 | 137 | 167 |

Grafting POLYOX 205 with Z6030 silane provides for a crosslinkable structure with good absorbency for water, saline, and simulated menses. The excellent dry film properties previously obtained with grafted PEO are retained when Z6030 is used as the grafting monomer. All films prepared with triethoxy vinyl silane remained water-soluble.

EXAMPLE 7

Another extrusion experiment was run as a control experiment without the addition of the peroxide initiator to confirm the graft chemistry described above. Without the peroxide initiator, the resulting material would be a blend of PEO and the Z-6030 monomer rather than a grafted copolymer.

Pelletized POYOX 205 was metered into the throat of the Haake extruder as described above at a rate of 37.8 g/min with a K-Tron feeder. Methacryloxypropyl silane (Dow Corning Z-6030 Silane) was metered into the throat of the extruder with an Eldex pump at a rate of 3.78 g/min, equivalent to ten weight percent of the POYOX 205. The temperature profile for the heating zones was 150°, 160°, 160°, and 170° C. The resultant strands were cooled in air using a fan-cooler conveyer belt. And the solidified strands of the grafted POLYOX 205 were then pelletized on a Conair pelletizer. A film was cast with a thickness of about 3 mils (0.76 mm).

Gel Fraction

A film sample from this experiment was conditioned at 37° C. and 80% relative humidity for 7 days. Gel fraction testing using the procedure described above resulted in gel content of less than two percent. In contrast, when the initiator is included to promote grafting of the alkoxysilane onto the PEO, the gel fraction under similar conditioning is typically more than 60 percent even with a shorter time of humidification.

EXAMPLE 8

Films were prepared from the modified PEO resins of Example 4 and the mechanical properties of the dry film were tested. The MD film properties in the dry state are shown in Table 15 below. The changes in properties that As the results indicate, crosslinking provides for improved film properties. Significant improvements are evident for break stress and energy to break. An increase in modulus is also evident, but the modulus does not increase to levels that are much different from HEMA-grafted PEO, with a modulus of about 165 Mpa. The high strain at break is not negatively impacted by the crosslinking reaction.

EXAMPLE 9

Films were prepared from the modified PEO resins of Example 5.

Gel fraction results after 26 and 165 hours at 33° C. and 89% relative humidity are shown in Table 16 below, along with results for gram-per-gram uptake of 0.9% saline.

TABLE 16

| FILM | RESIN SOURCE | RPM | WT. % PEROX-IDE | 26 HOUR GEL FRAC-TION | 165 HOUR GEL FRAC-TION | 165 HOUR G/G UPTAKE |
|---|---|---|---|---|---|---|
| 9-1 | 5-1 | 300 | .22 | 40 | 68 | 19.4 |
| 9-2 | 5-8 | 300 | .22 | 18 | 58 | 16.9 |
| 9-3 | 5-2 | 100 | .22 | 68 | 74 | 17.6 |
| 9-4 | 5-9 | 100 | .22 | 57 | 80 | 14.2 |
| 9-5 | 5-4 | 300 | .13 | Not tested | 50 | 22.2 |
| 9-6 | 5-7 | 300 | .13 | 14 | 65 | 21.2 |
| 9-7 | 5-3 | 100 | .13 | 77 | 83 | 19.3 |
| 9-8 | 5-6 | 100 | .13 | 81 | 75 | 14.8 |
| 9-9 | 5-5 | 200 | .17 | 79 | 84 | 13.7 |

The results indicate a significant effect of screw rpm and a minimal effect of peroxide level. Note that low screw rpm, which results in a longer residence time, produces a greater gel fraction, presumably as a result of higher grafting.

In general, the data from the extended cure time follows the same pattern observed after 26 hours of cure. The screw rpm (residence time) had the largest impact, while the peroxide level had little effect. Note that there is an overall increase in the gel fraction with the additional cure time.

The results for g/g uptake suggest that the capacity of the crosslinked PEO is increased with a lower level of crosslinking. This inverse relationship between capacity and crosslink concentration is consistent with the trends observed with polyacrylate super absorbents and also with PEO crosslinked with urethanes. The results also suggest that lower levels of the Z6030 crosslinking monomer under reactive grafting conditions that promote high grafting efficiency could provide for higher capacity at a lower cost. Therefore, for certain applications it is desirable that the polymer have a level of gel formation of about 2%–3% by weight; desirably, at least about 2% by weight. Such low levels of crosslinking may also be used to produce a polymer that has delayed water solubility or dissolution.

However, this uptake data is obtained under free swell conditions. For absorbency under load (AUL), a higher crosslink density may be needed. Therefore, for other applications it is desirable that the polymer have a level of gel formation of up to about 98% by weight. For other applications, it may be desirable to have a level of gel formation of about 50%–60% by weight.

An even more ideal structure would be similar to the shell crosslinked polyacrylates. This gradient in crosslinking might be achieved by surface application of a catalyst for the crosslinking reaction. Such a product would have a higher degree of crosslinking on the surface and a lower degree of crosslinking in the interior. Therefore, for certain applications it is desirable to have a level of gel formation of about 2% to about 60% by weight, and for other applications a level of gel formation of about 50% to about 98% by weight. The ability to vary the amount of gel formation provides the ability to select the properties that are desired in the final product.

EXAMPLE 10
Gel Fraction Under Ambient Aging Conditions

Film samples were stored in plastic bags under ambient laboratory conditions of temperature and the humidity available within the plastic bag. These conditions simulate the exposure conditions for films fabricated into a component of a personal care product that is packaged in a plastic bag. As shown in Table 17 below, the alkoxysilane grafted PEO crosslinks slowly under these storage conditions.

TABLE 17

| SAMPLE DESCRIPTION | RESIN SOURCE | STORAGE TIME | GEL FRACTION |
| --- | --- | --- | --- |
| 5% Z6030 .33% peroxide | 3-2 | 4 weeks | 32% |
| 5% Z6030 0.25% peroxide | 1-3 | 8 weeks | 52% |
| 5% Z6030 .33% peroxide | 3-2 | 18 weeks | 69% |
| 10% Z6030 .40% peroxide | 3-1 | 18 weeks | 70% |

EXAMPLE 11
Addition of Catalyst to Accelerate Crosslinking Reaction

The results obtained for samples prepared up to this time appeared to become fully crosslinked after about 7 days at elevated humidity and within 18 weeks under ambient, packaged storage conditions. Based on these results it is apparent that it may be even more desirable to create a crosslinked structure without exposure to high humidity or to require extended storage at ambient conditions. This objective could be met if a catalyst for the crosslinking reaction could be identified which could be added just prior to fabrication into the final structure. The catalyst should accelerate the crosslinking reaction so that crosslinking of the structure occurs under ambient storage conditions within the normal lag time between manufacturing and usage.

Resin pellets obtained from the second factorial experiment on the ZSK-30 PEO (POLYOX 205 reactively grafted with 7.3 weight percent Z6030) was coated with various levels of stearic acid by shaking the pellets and the stearic acid powder together in a plastic bag. Since there was not enough of any single sample to conduct the catalyst study, a composite sample was prepared by blending Samples 1–9 into a single "average" composition. Addition levels of stearic acid were 0, 0.1, 0.2, 0.4, 0.6 and 0.8 weight percent. The blends with stearic acid were prepared within four days of the reactive extrusion to minimize crosslinking during storage. Each blend was cast into a film using the HAAKE extruder under the conditions described above.

Film Observations and Gel Fraction

The results are show in the Table 18 below.

TABLE 18

| STEARIC ACID LEVEL | FILM CASTING OBSERVATIONS | GEL FRACTION AFTER 1 DAY OF AMBIENT STORAGE |
| --- | --- | --- |
| 0 | Smooth, thin film | 60% |
| 0.1 | Smooth, thin film | 55% |
| 0.2 | Smooth, thin film, slight torque increase | 47% |
| 0.4 | Smooth film, slightly thicker, higher torque | 81% |
| 0.8 | Rough film, thicker, higher torque | 96% |

The results above are somewhat obscured by the fact that the resin with no stearic acid added had a high gel fraction. (The gel fraction testing of Samples 1–9, which were combined for this study, was completed after the catalyst study). Nevertheless, the results indicate that addition of stearic acid at a level of at least 0.4%, is effective at increasing the gel fraction after just one day of storage under ambient conditions. However, the results also indicate that addition of excessive stearic acid causes difficulty in fabricating the resin into final form, presumably from premature crosslinking inside the extruder.

EXAMPLE 12

The resin from Example 6 (sample 6-1) was used to prepare monofilaments on a pilot-scale fiber spinning line. The spinning line consisted of two ¾ inch diameter 24:1 l:d (length:diameter) extruders with three heating zones which feed into a spin pump, through a ¾ Koch SMX static mixer unit and then into a spinpack, from which the monocomponent fibers were spun. The spinpack had 15 holes of 0.5 mm diameter.

The monofilament fibers were processed using the one extruder with a temperature profile of 170° C., 175° C., 180° C., 180° C., 180° C., 185° C., 185° C., for zones 1 through 3, melt pump, mixer and spinpack. The fibers were quenched at ~26° C. and collected in a freefall state (without draw down by a draw roll). The fibers were collected onto a spindle for testing.

Fiber samples were exposed to humid air (37° C. and 80% relative humidity) for one week and then tested for gel fraction according to the test method previously described. The fibers were found to have a gel fraction of 57% and absorbed 21 grams of water per gram of fiber.

The fibers displayed significant swelling in water. Fibers were cut to 25 mm in length and found to have a diameter of 0.38 mm in the dry state. After 30 minutes of immersion in water at room temperature, the fibers swelled to a length of 57 mm and the diameter increased to 2.0 mm. The dimensional changes observed were a length increase of 2.25 times the original length and an increase in diameter of 5.2 times the diameter of the dry fiber.

The series of foregoing Examples indicates that the material of the present invention has a unique combination of attributes: good absorbency for water, urine, and menses along with the capability to fabricate a wide range of structures using thermal processing. The ability to generate structures in a latent form (uncrosslinked) via melt processing coupled with a facile method to induce crosslinking into an absorbent material is very rare.

The absorbency properties of this new material are at an intermediate level between polyacrylate superabsorbents and cellulose pulp as shown in Table 19 below.

TABLE 19

| COMPARATIVE ABSORBENT PROPERTIES | CROSS-LINKED PEO | POLY-ACRYLATE SUPER-ABSORBENT | CELLULOSE PULP |
| --- | --- | --- | --- |
| Free swell absorbency | 12–25 g/g | 26–39 g/g | 3–6 g/g |
| Absorbency under 0.5 psi load | 8–14 g/g | 20–30 g/g | 2 g/g |

Another beneficial property provided by using PEO as a starting polymer is a low glass transition temperature. This attribute is particularly beneficial for personal care or medical products because the structures made from this material are soft and flexible—much like polyethylene or polypropylene which is commonly used to fabricate products in these markets. Plastic-like mechanical and fabrication properties along with good absorbency make this material highly unique. Some potential uses of the present invention are described below.

It is at the level of fabricated structures that the thermoplastic processability of the present invention opens up a wide range of potential structures. The present application describes simple films with good dry properties and high absorbency. When these films are placed in contact with fluid, they swell significantly (by a factor of about three times the original cross-machine direction). In addition, the films upon absorbing fluid are transformed from a plastic film to an even softer more compliant and unexpectedly elastomeric material.

Film applications are not limited to monolayer films. Also anticipated are multi-layer films (coextruded or microlayers). Films may be filled with particulate, such as polyacrylate superabsorbent particles, or mineral fillers, such as clay. The forms described may also be applied to blends composed of alkoxysilane-grafted PEO with other polymers. Also, a wide variety of laminated structures are possible. For example, films may be laminated with nonwoven structures, such as meltblown or spunbond. Laminates are possible with tissue webs or woven fabrics. Specifically, a layer of film in accordance with the present invention can be laminated between two nonwoven layers, such as sheets of tissue. Fibers in accordance with the present invention may be laminated with other structures or with other fibers made from the same or different material, such as pulp. Fibers can be laminated with films of the same or different material. Because the alkoxysilane-grafted PEO has a rather low melting point, the laminates may be fabricated by melt extrusion onto the other component or by applying pressure to both components as they passes through heated nips.

Because of the thermal processability of alkoxysilane-grafted PEO, the present invention may be used for fabricating foam structures. Thermally processed foam technology is widely practiced with polyethylene by utilizing chemical and physical blowing agents. Alkoxysilane-grafted PEO has properties similar to polyethylene so it is contemplated that the use of chemical blowing agents will also produce foam structures. However, unlike polyethylene foams, the foams made from alkoxysilane-grafted PEO should be highly absorbent. Extension of the foam technology to produce net-like structures is also anticipated. Laminates can also be formed from foam structures. Specifically, foams in accordance with the present invention can be laminated with films of the same or different materials.

It is expected that a wide variety of fibrous structures can be fabricated with the alkoxysilane-grafted PEO. Such fibrous structures include melt blown and spunbond nonwovens, as well as bicomponent fibers and structures made from them. Filaments that swell and become elastomeric when contacted with fluid are also possible. As previously indicated, such PEO materials can also be made into film coatings for various substrates. In this regard, the following set of examples focus on use of the PEO materials in various coatings.

When it is said that the coating is "absorbent", what is meant is that the coating/material can absorb water. As will be further shown in the Examples, which follow, the present coatings are capable of absorbing their own weight in water, or even many times their own weight. It is believed that this is an advantage of the present coatings, particularly when they are used in applications where moisture absorption and control are important—such as in bandages, wound dressings, and the like.

When it is said that the coating is "substantially non-water soluble", it is meant that the cured coating has a solubility in water at 25° C. of less than 40% by weight, desirably, less than 4% by weight.

EXAMPLE 13

This example illustrates the formation of a coating of the novel graft copolymer on silicone rubber.

A modified poly(ethylene oxide) was produced from poly(ethylene oxide) (Polyox WSR-205 resin, available from Union Carbide) grafted with 3% by weight of methacryloxypropyl trimethoxy silane (Dow Corning Z-6030 Silane, available from the Dow Corning Co.) in the presence of a peroxide initiator (Varox DBPH, supplied by R. T. Vanderbilt Co., Inc.) as described in Examples 1–6, above. A 2% by weight solution of this material was prepared by the addition of the dry copolymer to a suitable amount of water with stirring at room temperature. A portion of the solution was poured into a silicone rubber mold having a rectangular depression 2 mm deep. The solution was dried overnight at room temperature to provide a smooth film that became lubricious when re-wetted. The film adhered tenaciously to the surface of the silicone rubber.

EXAMPLE 14

This example illustrates the formation of a lubricious, absorbent coating on several different fibers and fabrics.

A modified poly(ethylene oxide) was produced from poly(ethylene oxide) (Polyox N-80 resin, available from Union Carbide) grafted with 6% by weight of methacryloxypropyl trimethoxy silane (Dow Corning Z-6030 Silane, available from the Dow Corning Co.) in the presence of a peroxide initiator (Varox DBPH, supplied by R. T. Vanderbilt Co., Inc.) as described in Examples 1–6, above. A 3% by weight solution of this material was prepared by the addition of the dry copolymer to a suitable amount of water with stirring at high shear using an Ultra Turrax mixer (available from IKA Laboratory Technology with offices in Wilmington, N.C.) at room temperature. This solution was used to saturate the following fabrics: (1) 0.45 ounces per square yard (osy) wettable spunbond diaper liner (available from Kimberly-Clark Corporation, Neenah, Wis.), (2) rayon bonded carded web (composed of 50% rayon and 50% polypropylene/polyethylene bicomponent binder fiber (BCW) (available from Kimberly-Clark Corporation, Neenah, Wis.), and (3) poly(lactic acid) (PLA) fiber surge material (available from Kimberly-Clark Corporation, Neenah, Wis.). The coated substrates were dried at 50° C. overnight. The weight percent of coating that was deposited upon each of the dried materials was determined, and each material was tested for saline uptake under 0.5 psi load (as described in the General Procedures, above). The results are shown in Table 20.

Table 20: Weight percent coating and amount of saline uptake for fabrics coated with 3% graft copolymer.

| SUBSTRATE | WEIGHT PERCENT COATING | SALINE UPTAKE AT 0.5 PSI LOAD (G/G) |
|---|---|---|
| 0.45 OSY Wettable Spunbond | 51% | 4.2 |
| Rayon BCW | 30% | 4.8 |
| PLA Surge Material | 32% | 10.8 |

The results illustrate that relatively inexpensive, readily available substrates can be coated with cross-linked modified poly(ethylene oxide) copolymer to form a hydrogel coating that is very absorbent in an aqueous fluid.

EXAMPLE 15

This example illustrates the formation of a lubricious, absorbent coating on PLA surge material.

A modified poly(ethylene oxide) was produced from poly(ethylene oxide) (Polyox N-80 resin, available from Union Carbide) grafted with 6% by weight of methacryloxypropyl trimethoxy silane (Dow Corning Z-6030 Silane, available from the Dow Corning Co.) in the presence of a peroxide initiator (Varox DBPH, supplied by R. T. Vanderbilt Co., Inc.) as described in Examples 1–6, above. A 7% by weight solution of this material was prepared by the addition of 28 g of the dry copolymer to 372 g of water with stirring at 11,000 rpm for 30 minutes using an Ultra Turrax mixer (available from IKA Laboratory Technology) at room temperature. This solution was placed in a dish on a sample of surge material (P-6951-82-1) made from PLA staple fiber. Pressure was applied to force the viscous solution into the surge structure. Excess solution was wrung out and the sample was dried for four hours at 50° C. The coating increased the weight of the fabric by an average of 62%. The coated surge sample quickly absorbed saline solution and retained 8.6 g/g of saline under 0.5 psi load.

EXAMPLE 16

This illustrates the efficacy of various fabrics coated with the novel absorbent poly(ethylene oxide) co-polymer for absorption of saline solution and wound fluid.

Several different substrate materials were coated with a copolymer produced from POLYOX N80 with 6% by weight engrafted Z6030 monomer by the method described in Examples 13 and 14, above. Table 21 shows the substrates that were coated and the weight percent of the dry copolymer coating that was retained on the fabric. Each of the coated materials was then tested for uptake of 0.9% saline retained under 0.5 psi weight, as described in the General Procedures, and for the absorption of wound fluid by the fluid handling capacity test for wound dressings. This test is described in the British Pharmacopoeia 1993, Addendum 1996, available from the British Pharmacopoeia Commission, London, UK. The simulated wound fluid used for this test consists of sodium chloride and calcium chloride solution containing 142 mmol of sodium ions and 2.5 mmol of calcium ions as the chloride salts. This solution has an ionic composition comparable to human serum or wound exudate. It is prepared by dissolving 8.298 g of sodium chloride and 0.368 g of calcium chloride dihydrate in deionized water and making up to 1 liter in a volumetric flask.

TABLE 21

Efficacy of various fabrics coated with the novel cross-linked modified poly(ethylene oxide) co-polymer for the absorption of saline solution and wound fluid.

| COATED SUBSTRATE | WEIGHT PERCENT COATING | UPTAKE OF 0.9% SALINE AT 0.5 PSI (G/G) | WOUND FLUID ABSORBED (g/g) | FLUID HANDLING CAPACITY TOTAL WOUND FLUID HANDLED PER 100 cm² OF DRESSING (g) |
|---|---|---|---|---|
| PLA BCW Surge | 32% | 10.8 | 18.6 | 33 |
| Polypropylene BCW Surge | 45% | 16.7 | 19.8 | 38 |
| Rayon BCW | 30% | 4.8 | 13 | 14 |
| Spunbond polypropylene 0.45 osy | 50% | 4.2 | 6.4 | 10 |
| SigmaDress hydrocolloid dressing | | | | 16 |
| ConvaTech Duoderm Hydrocolloid Dressing | | | | 15 |
| Dow Hickam Flexderm Hydrogel Dressing | | | | 24 |

These results indicate that fabrics coated with the novel cross-linked modified poly(ethylene oxide) co-polymer have equivalent or greater absorbent capacity as commercially available hydrocolloid wound dressings along with much greater mechanical integrity in the saturated condition. The commercial products in the table above were tested with the same method. A measure of g/g wound fluid absorbed is not included because these products have integral cover materials that cannot be removed without damaging the dressing. Therefore an accurate weight of the actual absorbent portion was not obtained. If the cover weight is included the g/g absorbency for all these products is less than 2 g/g.

EXAMPLE 17

This illustrates the preparation of a lubricious coating from an organic solvent. A modified poly(ethylene oxide) was produced from poly(ethylene oxide) (Polyox N-80 resin, available from Union Carbide) grafted with 6% by weight of methacryloxypropyl trimethoxy silane (Dow Corning Z-6030 Silane, available from the Dow Corning Co.) in the presence of a peroxide initiator (Varox DBPH, supplied by R. T. Vanderbilt Co., Inc.) as described in Examples 1–6, above. A 2% by weight solution of this material was prepared by the addition of 2 g of the dry copolymer to 98 g of acetonitrile with stirring at 11,000 rpm for 4 minutes using an Ultra Turrax mixer (available from IKA Laboratory Technology) at room temperature. 19.8 grams of this solution was combined with 28 grams of 2-butanone and 1 gram of water to provide a total resin concentration of 0.8%. A 9 cm sample of silicone rubber tubing (outer diameter 0.9 cm, inner diameter 0.6 cm, obtained from Ballard Medical of Kimberly Clark) was dipped into the solution and dried at 5° C. for 15 minutes. Two additional coatings were applied in the same manner, a total of three coating applications. The coated silicone tubing was non-tacky in the dry state. When the coated silicone tubing was immersed in water or 0.9% saline solution the coating became hydrated to provide a lubricious surface. Alternatively, the coating can imbibe water from body fluids, even if it is not exposed to water prior to introduction into the body. The coating retains its lubricating properties even after subsequent drying and rehydration.

EXAMPLE 18

This illustrates the controlled delivery of various therapeutic materials that were incorporated into the novel absorbent poly(ethylene oxide) co-polymer. A solution cast film was prepared by blending 2% (by weight) aqueous solutions in a 60:20:20 weight ratio of the following components: Polyox 205 (Union Carbide) with six weight percent of Dow Corning Z-6030 grafted thereonto; chitosan malate, and glycerin. The solution blend was poured into a polypropylene weighing dish. The water was evaporated at 50° C. for four hours to provide a thin, flexible, translucent film that contains at least 40% by weight water-soluble therapeutic materials. Similarly, a solution cast film was prepared by blending 2% (by weight) aqueous solutions of the following components: Polyox 205 (Union Carbide) with three weight percent of Dow Corning Z-6030 grafted thereonto with chitosan malate in a 60/40 weight ratio.

Alternatively, a film with therapeutic materials incorporated was prepared by "loading" a film in the following manner. A melt cast film was made of Polyox 205 (Union Carbide) with seven weight percent of Dow Corning Z-6030 grafted thereonto and then exposed to humid air to provide a cross-linked film with an absorbent capacity of approximately 9 grams per gram of dry film. A solution blend was prepared consisting of 97 grams of aloe vera solution (0.76% by weight) with 3 grams of glycerin. 24 grams of this solution blend was poured into a petri dish and the crosslinked film described above, which weighed 2.66 grams in the dry state, was place into the solution blend. The film swelled and absorbed the solution within five minutes to produce a film gel that contained the aloe vera and glycerin. The swollen film gel was placed between two fiberglass screens and dried at 50° C. for four hours. The resultant dry film had an estimated composition of 75% grafted copolymer, 20% glycerin, and 5% aloe vera (a therapeutic agent beneficial for treating burns).

The coated polypropylene surge was prepared as describe in EXAMPLE 15. by blending 37.5 g 3% (by weight) aqueous solutions of Polyox 205 (Union Carbide) with six weight percent of Dow Corning Z-6030 grafted thereonto; 1 gram of 30% glycerin solution and; and 9.9 gram of 1% aloe vera solution. This blend solution was placed in a dish on a sample of surge material made from polypropylene and polyester staple fiber. Pressure was applied to force the viscous solution into the surge structure. Excess solution was wrung out and the sample was dried for four hours at 50° C. The coating increased the weight of the fabric by 46 percent. A second coated surge material was made in exactly the same manner except a 3% (by weight) aqueous solutions of Polyox N80 (Union Carbide) with six weight percent of Dow Corning Z-6030 grafted thereonto was used. The coating increased the weight of the fabric by 44 percent.

To test the capability of the novel absorbent poly(ethylene oxide) co-polymer to deliver various therapeutic materials that were incorporated into the structure, an extraction experiment was done in the following manner. Weighed samples of the film or coated substrate with compositions indicated in Table 22, were immersed for 15 minutes in 200 g of 0.9% saline solution at 37° C. for 15 minutes. This condition was chosen to simulate exposure to excess body fluid at body temperature. The samples were dried overnight at 50° C. and reweighed to determine the amount of material released from the sample. The results indicated that as the composition swells and absorbs the simulated body fluid at least a portion of the water-soluble component is released from the film or coating.

As described above, the therapeutic compounds can be combined into a film or coating with the novel co-polymer by multiple methods. The advantage is that such therapeutic materials can be incorporated into a coating, and the coating will then act to release the material over an extended period of time when the coating is exposed to body fluid, for example wound exudate. The solubility of the therapeutic material, the loading level of the therapeutic material, and the rate of swelling of the novel co-polymer can control the rate and amount of the therapeutic material released. Methods known in the art for controlling release rate from hydrogels by controlling the rate of fluid intake by means of blending or coating the surface are also anticipated.

TABLE 22

Delivery of therapeutic materials incorporated into films and coatings formed from the novel absorbent poly(ethylene oxide) co-polymer.

| MATERIAL | COMPOSITION[A] | THERAPEUTIC MATERIAL RELEASED (WT. %) | THERAPEUTIC MATERIAL REMAINING (WT. %) |
|---|---|---|---|
| Solution cast film | 60/20/20: 205-6 Copolymer/ Glycerin/ Chitosan malate | 64% | 36% |
| Solution cast film | 60/40205-3 Copolymer/ Chitosan | 100% | 0% |
| Loaded Film | 75/20/5: 205-7 Copolymer/ Glycerol/ Aloe vera | 77% | 23% |
| Coated Polypropylene Surge | 75/20/5: 205-6 Copolymer/ Glycerol/ Aloe vera | 45% | 55% |
| Coated Poly- | 80/20/5: N80-6 | 55% | 45% |

TABLE 22-continued

Delivery of therapeutic materials incorporated into films and coatings formed from the novel absorbent poly(ethylene oxide) co-polymer.

| MATERIAL | COMPOSITION[A] | THERAPEUTIC MATERIAL RELEASED (WT. %) | THERAPEUTIC MATERIAL REMAINING (WT. %) |
|---|---|---|---|
| propylene Surge | Copolymer/ Glycerol/ Aloe vera | | |

Notes:
[A]Numbers such as 60/20/20 give the parts by weight of the listed components in the cross-linked hydrogel. The designation 205-3 and 205-6 mean that the poly(ethylene oxide) resin that was used in the synthesis of the absorbent co-polymer was Polyox 205 (Union Carbide) and the weight percent of Dow Corning Z-6030 grafted thereonto was, respectively, 3% by weight, or 6% by weight, based on the poly(ethylene oxide). The designation N80-6 means that the poly(ethylene oxide) that was used in the synthesis of the absorbent co-polymer was Polyox N-80 (Union Carbide), and the weight percent of Dow Corning Z-6030 grafted thereonto was 6% by weight, based on the poly(ethylene oxide).

As has been demonstrated the materials of the foregoing examples may be placed in a film or fibrous structure or may be coated onto such a structure in order to serve an absorbent component.

Such absorbent component is desirably an absorbent component in a bandage. Such a bandage may itself be adhesive bandage, or in the alternative, a bandage that may require adhesive tape for its application, or be in the form of a wound dressing. Such absorbent component allows for continued absorbency despite the compression that it may be exposed to as part of a bandage. Furthermore, such component will allow for the release/transfer of wound healing compounds to a wound, such as niacinamide ascorbate. The material may be extruded as fibers in order to make an absorbent web-like material for use as an absorbent pad. In the alternative, the material may be extruded as a film, in order to make an absorbent pad of an adhesive bandage or a coating for an absorbent pad of a bandage. Still, in a further alternative embodiment, the absorbent coating may be applied to a perforated nonstick barrier layer over an absorbent pad within a bandage/wound dressing.

As has been previously indicated, the copolymers described above can be used to form a coating on an article, the method involving contacting the article with a copolymer of a water soluble base polymer having graft polymerized thereto an organic moiety that includes a group that reacts with water to form a silanol group; and curing the copolymer to form a coating comprising the crosslinked copolymer on the article.

In one embodiment, the method for contacting an article to be coated with the copolymers described above is to form a solution of the copolymer in a solvent and place a film of solution on the article. As that term is used herein, "solution" should be understood to include true solutions, emulsions and dispersions.

It is believed that this coating solution is also within the scope of the present invention. The coating solution comprises a mixture of a solvent and a copolymer comprising a water soluble base polymer having graft polymerized thereto an organic moiety that includes a group that reacts with water to form a silanol group. The water soluble base polymers and organic moieties that are useful for the present coating solutions include those that have been discussed above. In particular, solutions containing poly(ethylene oxide) engrafted with 3-methacryloxypropyl tris (methoxyethoxy) silane have been found to be desirable.

When the copolymer is placed into solution in a solvent, it is believed that almost any liquid can be used. It is desirable that the liquid be an organic solvent, such as an alcohol, ketone, aldehyde, alkane, alkene, aromatic, or mixture thereof, or be water. Water can also be used in combination with an organic solvent. When a mixture of water and an organic solvent is used as the solvent, the water should be present in an amount of from about 5% to about 100% by weight. It is desirable that pure water be used as the solvent.

Variable amounts of the copolymer can be used to form the solution. It is believed that solutions containing from about 0.1% to about 10% by weight of the copolymer can be used, and solutions containing about 1% to about 8% by weight are desirable in some instances. Still in a further alternative embodiment, solutions containing about 1 to about 6% by weight are desired. Still, in even a further alternative embodiment, solutions containing about 1 to about 4% by weight are desired.

After the copolymer has been placed into solution in a solvent, the solution is then contacted with the article to be coated so as to place a film of the solution on the article. This can be done by dipping, spraying, printing, painting, or immersing the article with or in the solution. A common way to apply the film to the article is to simply dip the article into the solution and allow any excess solution to drain from the article. This step can be carried out once, or it may be repeated any number of times. If desirable, the copolymer in the film may be cured after a film has been applied, and then the application of another film of the copolymer may be repeated in order to build up a coating of the desired thickness.

After a film of the solution containing the copolymer has been applied to the article, the copolymer is cured to form a cross-linked hydrogel coating. The copolymer can be cured by removing solvent from the copolymer. One method of removing liquid that results in curing the copolymer is to evaporate the solvent. A common method for carrying out the evaporation is by drying the article. Such drying is commonly done in air under ambient conditions, but the article can be placed in an oven or other temperature and/or humidity controlled space in order to control the drying. As the solvent is removed from the film, silanol groups of adjacent copolymers form bonds to cross-link the structure into a hydrogel.

As an alternative, removal of the solvent can be carried out by any method, such as, for example, absorption, chelation, sequestration or chemical reaction.

In an alternative method, the coating can be applied to the article by applying a film of liquid to the article, where the film contains the copolymer in un-crosslinked form. This can be done by melting the copolymer and applying the molten copolymer to the article to form the film. Alternatively, the copolymer may be dispersed in a non-aqueous solvent to form a dispersion or emulsion, and the dispersion or emulsion can be applied to the article to form the film.

When the un-crosslinked copolymer is used to form a film on an article it is normally desirable that this be carried out under substantially water-free conditions in order to avoid premature cross-linking of the copolymer. In fact, it is often desirable that the film be applied under conditions that are substantially anhydrous.

It is normal for the film that is applied to the article to be coated to be applied in such a manner that it substantially covers the exterior surface of the article, such as the absorbent, or perforated film barrier. Of course, when a coating is to be placed on the interior surface of an article, it is necessary that the film also contact that surface. In fact, any surface that is to be coated should be covered by the film.

After the film containing the un-crosslinked copolymer has been applied, it can be cured by contacting the film with water. This can be done in any manner, such as dipping, spraying, misting, or exposing the article to high humidity conditions. When it is said that the article is to be contacted with water, any form of water is included—such as liquid water or water vapor.

One important characteristic of the curing step of the novel coating method is that it is free of the need for the use of ionizing radiation, such as gamma radiation. It can also be done at ambient temperature and pressure. Moreover, it can be carried out at normal, physiological pH values, for example, at a neutral pH, or at a pH between about 6 and about 8. Benefits of this feature include that the curing can be done while the film is in contact with a wound, and that there are no residual fluids having biologically irritating low or high pH values that could leach out of a dressing and irritate a wound.

The copolymer is cured by the method described above to form a coating on an article, the coating comprising a crosslinked hydrogel that includes a copolymer comprising water soluble base polymers having graft polymerized thereto organic moieties that react with water to form a silanol group, the copolymer being crosslinked through the silanol groups of the organic moieties to form a coating that is absorbent, lubricious and substantially non-water soluble.

As can be seen in FIG. 2, for use in a bandage, the present invention is generally directed to a bandage 60 for acute wounds, consisting of a base sheet 70 having a bottom side surface 75 and a top side surface 76 which is that surface seen by a consumer after application of the bandage to the wound site. In one embodiment, the base sheet is desirably elastomeric. In a further embodiment, the base sheet has been coated with a suitable skin-friendly adhesive 77, along its skin contacting surface (bottom side surface 75). It should be appreciated that this is not necessary if it is not desired that the base sheet be applied to a wound via its own adhesive. In this instance, separate adhesive tape may be used. The elastomeric base sheet may be comprised of nonwoven and film-based polymeric materials or combinations thereof, for example, such as those materials described in U.S. Pat. Nos. 3,976,563 and, 5,633,070 which are incorporated by reference herein in their entirety. Such base sheets are made by methods known in the art, and described in the heretofore mentioned patents. The elastomeric base sheet may be a breathable monolithic film or a perforated film, to provide for some level of flexibility around a joint (if appropriate) and some level of breathability. Alternatively, the base sheet/backing material may be a nonwoven material, or a combination of a nonwoven material and a film. If present, the adhesive may be any skin-friendly adhesive known in the art, such as rubbery adhesives, acrylic adhesives, polyurethane adhesives, silicone adhesives, and block copolymer adhesives and those described in U.S. Pat. Nos. 4,147,831, 4,551,490, and EPO 361 722B1, EP 1008330A2, and WO 00/12038 which are incorporated by reference herein in their entirety. The base sheet includes along its skin contacting surface (bottom side layer), an absorbent layer 80 (or absorbent pad). In one embodiment, the absorbent PEO materials of the present invention may make up the absorbent layer or coat the absorbent layer in a film coating. If the inventive composition is used to coat such absorbent pad, such pads are those as described in the previous references. Desirably, the PEO materials include a hemostatic agent, and desirably an antimicrobial/wound healing agent associated therewith. Desirably, the absorbent layer is composed of blends of crosslinked poly(ethylene oxide), that have been modified by grafting with an alkoxy silane functional group, along with a chitosan salt (hemostatic agent) and a the healing agent niacinamide ascorbate associated therewith.

In one embodiment, the absorbent layer can be a thin film of this composition. By thin, it is desirable that the thin film be between about 0.01 mm and 0.3 mm. More desirably, the thin film is between about 0.02 mm and 0.1 mm in thickness.

In the embodiment with a separate absorbent layer, the absorbent layer may be a thin substrate that has been coated with this composition. For example, such a thin substrate may be composed of a polypropylene spunbond nonwoven material, a rayon bonded, carded web, a polyester bonded carded web, or cotton gauze. The coating on such a substrate may be about 0.1 mm in thickness and may be produced by saturating the substrate with a solution comprising crosslinked poly(ethylene oxide), that have been modified by grafting with an alkoxy silane functional group, and beneficial wound healing agents (exemplified by chitosan niacinamide ascorbate and niacinamide ascorbate), followed by removal of the solvent to deposit the coating onto the substrate.

In still a further embodiment of the present invention, a third layer may be in contact with the wound, 85. Such a layer may be a perforated nonstick film layer, such as a Delnet polyethylene film, available from AET of Delaware. The PEO material of the present invention may in an alternative embodiment coat such perforated layer as seen as 90 in FIG. 2. In a further alternative embodiment, the PEO and chitosan-based materials may be in the absorbent layer and the separate antimicrobial/wound healing agent can be on the surface of the perforated nonstick layer for transfer to the wound.

In use, such an absorbent layer, when exposed to aqueous fluids, forms a highly absorbent gel that releases the hemostatic, antimicrobial and wound healing agents to the wound. The manufacture of bandage materials is known in the art, and such lamination and/or manufacturing methods are described in the cited references.

Several hemostatic agents were compared to determine relative effectiveness when reviewed with untreated human blood. Such comparison is illustrated in the following Table 23.

Table 23

Each of the compounds were evaluated in the comparison against the standard control (human blood) and the negative control heparin, which is an anti-coagulant. The results of the study are shown in Table 23 which follows. As can be seen in the data of Table 23, Chitosan niacinamide ascorbate produced the shortest coagulation time of any of the compounds evaluated.

Preliminary Review of Hemostatic Agents
Lee and White Coagulation Assay in Human Blood

TABLE 23

| COMPOUNDS | BLOOD CLOTTING TIME (MIN) |
| --- | --- |
| Chitosan niacinamide ascorbate | 8.83 ± 0.28 |
| Chitosan | 9.00 ± 0.50 |
| Sodium alginate* (Granular, Aldrich) | 9.33 ± 0.28 |
| Untreated blood (control) | 10.16 ± 0.28 |
| Heparin (negative control for comparison) | NC |

NC = No Clot for 60 min
All tests were run in triplicate and samples were used in dried form (5 mg/ml)

Study of Control Bandage Material and Test Compounds

Following the assessment of hemostatic agents, a study was conducted using the accelerated wound healing study protocol which follows. In the examples of the study, a series of comparative control bandage substrates were evaluated as to the speed at which wounds covered/dressed with such bandages healed. In particular, the rates of re-epithelialization were measured for wounds dressed by such control dressing materials. Additionally, the rates at which wounds heal that have been treated with a series of test compounds in accordance with the present invention, were also measured and compared with the controls.

For the purposes of the examples, the test compounds consisted of Chitosan, Niacinamide ascorbate (hereinafter NA) prepared by the method which follows; and chitosan niacinamide ascorbate salt (hereinafter CAN, prepared by the method which follows), 2-ply surgical gauze, and Comfeel® Plus Clear Dressing (Colorplast).

Wounds were treated with test and control articles on the day of wounding (day 0) on 2,4,6,8,10, 12, and 14 days after the injury. CNA (freeze dried) was cut to the approximate size of the wound and applied over the wound. Chitosan (powder) and NA (powder) were applied over the wound to the depth that covered the underlying tissue. The gauze was cut to extend approximately 0.5 cm beyond the margins of the wound. The Comfeel® Plus dressing was cut to the approximate size of the wound and applied over the wound and also used to cover all test and control articles over the entire dorsal surface of the animal.

Specifically, these examples illustrate the effects of test compounds on wound healing in a rat model, as described in J. M. Davidson, *Arch Dermatol Res.*, 290 (Suppl): S1–S11, 1998; J. P. Heggers et al., *J Altern Compl Med.*, 2,271–77, 1996; J. A. Hokanson et al., *Wounds*, 3, 213–220, 1991, which describe such testing protocols, and which are incorporated herein by reference in their entirety.

For the study, twenty four albino rats (12M/12F), each weighing between 250–300 g, were anesthetized (90 mg/Kg Ketamine HCL and 10 mg/Kg Xylazine) and the entire dorsal region of each rat was shaved. Four wounds measuring 1.4 cm$^2$ were made on the dorsal skin, two on either side of the vertebral column, with a rotary dermabrasion device (Dermatome). The wounds were made to a depth to yield full thickness (excisional) wounds. The test compounds and control bandages were applied topically to cover the entire wound. Test compounds and control dressings were distributed among three animals of each sex per time point (1,2,5,10,15 days), such that each test and control was applied twice/sex/time point. Four rats (2M/2F) were sacrificed at each time point and morphometric analysis was used to assess the re-epithelialization of each wound at each time point. At each time of sacrifice, each wound was excised with 5 mm margin of uninjured tissue as a border. Sections were cut in cross sections encompassing the entire wound and began at the margin of the initial wound and proceeded in 3.5 mm increments across the width of the wound. The epithelial thickness of the three sections of the wound (margin, center and midpoint between these two) was measured by morphometric analysis of the microscopic image using Image-Pro Plus software, Version 3.0 (Media Cybernetics). The average thickness of these sites within the wound was determined for wound healing of the entire site. The rate of epithelialization at the test and control sites was plotted vs time and presented in FIGS. 3–10.

Preparation of NA and CNA for the Study

Niacinamide ascorbate (0.87 g, 0.0029 moles) was prepared by mixing equimolar amounts of niacinamide (Sigma Chemical) and ascorbic acid (Sigma Chemical) as reported earlier by C. W. Bailey et al., *J Amer. Chem. Soc.*, 67, 1184–5, (1945), was dissolved in 60 ml $H_2O$ (pH of 3.85 at 20.9° C.). The solution was stirred for ten minutes and chitosan (0.5 g, degree of deacetylation 78.8%, 0.0029 moles) was added to the solution. The solution was stirred for 3 hrs to give a clear solution (pH of 4.62 at 21.4° C. of chitosan niacinamide ascorbate salt (CNA)). The pH of the solution was adjusted to 5.6 by adding chitosan (0.4 g) in 20 ml water. The material was dried by freeze drying. It should be noted that NA is also commercially available commercially from the Spectrum Chemical. Following completion of the study, the data was analyzed and graphed as follows.

Results of Study

FIG. 3 is a graph illustrating a graph showing accelerated wound healing in the full thickness acute wound model, showing the epithelial thickness of rats over a period of 15 days. In the graph, the rate of epithelialization in thickness (microns) is compared for five materials, include the two controls gauze and Comfeel®, and the test compounds Chitosan, CNA and NA. The evaluation of thickness change was monitored over a period of 15 days. As can be seen from the study, the compounds Chitosan, CNA and NA each dramatically increased the wound healing capability in rats over standard gauze bandages as well as other commercially available treated bandages. As a result, it is expected that such antimicrobial and hemostatic materials will provide similar benefits in PEO inclusive bandage of the present invention.

Desirably, the range for the grafting level of the alkoxy silane in the PEO material is within the range of about 0.5 to about 10 weight percent, relative to the weight of the poly(ethylene oxide). It has been determined that resins with higher grafting levels produce a stiffer gel with high lubricity and less absorbent capacity, while lower grafting levels produce softer, more absorbent gels on the surface of the substrate.

Desirably, the ranges of chitosan in the bandage are between 0.01% and 75% by weight of the absorbent film or coating. Desirably, the ranges of chitosan in the bandage are between 5% and 55%. More desirably, the ranges of the chitosan in the bandage are between 15 and 55%. Still, even more desirably, the ranges of the chitosan in the bandage are between 25 and 45 by weight (all are of the absorbent material with the PEO). Such chitosan material is available from Vanson, Inc., Remond, Wash. Desirably, the range of niacinamide ascorbate in the bandage is between about 0.1 and 70% by weight of the dry film, if it is a part of the absorbent layer. If it is in a separate layer, such as on the nonstick perforated film layer, the percent can be between 0.001 and 90%, of the treatment on that other layer. Desirably, the ratio range of niacinamide to ascorbate is between 20:1 to 1:10. The niacinamide ascorbate is available from Spectrum Laboratories Products Inc, of Gardena, Calif.

It should be noted that the resin pellets are manufactured in the reactive extrusion process as previously described. The solution of the poly(ethylene oxide), that has been modified by grafting with an alkoxy silane functional group is prepared by dissolving the resin pellets in water with the aid of Ultra Turrax high speed mixer/homogenizer. In an alternative embodiment, the resin concentration of poly (ethylene oxide), that has been modified by grafting with an alkoxy silane functional group range can be between about 0.1 to about 6 weight percent, as higher concentration solutions tend to gel more quickly. Choice of concentration is dictated by the viscosity requirements of the method of application and by the available time between solution preparation and the on-set of gellation resulting from moisture-induced crosslinking. Solution concentrations at or above about 4% begin to gel in less than an hour while solutions of 2% are free of noticeable gelling for days. Suitable application methods for the material as a coating include saturation, knife coating, spray, spray drying, and printing, such as through gravure, ink jet or screen printing.

Another feature of the present coating is that it can act as a reservoir for other releasable components that are to be delivered from the coating to a region outside of the coating, such as, for example, a wound. In this embodiment, the coating can act to provide a controlled release of such compounds as therapeutic agents, bioactive agents, antibiotics, bactericides, fungicides, drugs, growth factors, peptides, proteins, enzymes, emollients, antiseptics, antioxidants, wetting agents, and mixtures thereof.

EXAMPLE 19

The resin compositions of the example to follow were obtained from reactive grafting of poly(ethylene oxide) with 6% by weight of trimethoxysilyl propylmethacrylate. Such PEO resins are commercially available from, for example, Union Carbide Corporation having offices in Danbury, Conn., and are sold under the trade designation POLYOX® 205

The compositions in the example of this invention were prepared at 4% by weight poly(ethyleneoxide) grafted with 6% by weight alkoxysilane. A 2% solution of chitosan malate was prepared by deionized water using the Ultra Turrax high speed mixer. Some of the compositions shown in Table 24, which follows, contained glycerine which was added as a 4% solution in deionized water. The glycerine humectant is incorporated into the composition to make the film softer (lower modulus) and to provide moderate elastomeric properties. Such material provides a moist environment for wound healing, while still allowing for absorbency. The niacinamide ascorbate was prepared as previously described and mixed into the solution prior to evaporation so as to allow the NA to become entrapped in the polymeric matrix.

TABLE 24

| ALKOXY-SILANE-GRAFTED PEO | CHITOSAN MALATE | % GLY-CERINE | NA | G/G FREE SWELL UPTAKE | % RE-LEASED |
|---|---|---|---|---|---|
| 40 | 35 | 20 | 5 | 12 | 100 |
| 40 | 40 | 15 | 5 | 22 | 97 |
| 50 | 25 | 20 | 5 | 11 | 100 |

For the abbreviations in Table 24 above, alkoxysilane-grafted PEO represents uncrosslinked alkoxysilane-grafted polyethylene oxide in percent by weight of the dry film composition. Chitosan Malate is in percent by weight of the dry film composition. Percent glycerine is percent by weight of the dry film composition. NA represents niacinamide ascorbate. The abbreviation g/g represents grams per gram of the dry film. The term "% (percent) released" represents the percent of the available water-soluble materials (niacinamide ascorbate and glycerine) released from the absorbent pad. Note that the alkoxysilane grafted PEO becomes crosslinked during the drying process such that the alkoxysilane grafted PEO and the chitosan malate are no longer appreciably water-soluble.

Free swell uptake in the examples was determined by immersion of a dry film of the material in water at 37° C. for 30 minutes. The film was prepared by pouring the solution blend into a polypropylene weighing dish and drying at 50° C. in a forced air oven. The recovered swollen gel was blotted to remove surface moisture and weighed to determine the uptake. The swollen gel was then re-dried at 50° C. overnight in the forced air oven and reweighed to determine the % weight loss or % of soluble components released.

The data from Table 24 indicates that the combination of alkoxysilane grafted PEO with chitosan malate provides an ample level of absorbency in the free swell condition. Furthermore, the results indicate that the, glycerin and the niacinamide ascorbate is released from the film.

Still other examples of material substrates that can be coated with alkoxysilane grafted PEO solutions or blends to provide an absorbent coating upon drying include 0.45 osy wettable spunbond nonwoven material with 30% by weight of dried coating, and HICap surge material (manufactured by Kimberly-Clark Corp.) with 42% by weight of dry coating. This invention is a particular refinement to provide a new composition with absorbent properties and delivery capability.

Chitosan is reported in the Journal of Applied Polymer Science 74: 2911 (1999) to provide antimicrobial properties when applied to a polypropylene nonwoven fabric. The applications of the solutions described in this disclosure are expected to provide similar antimicrobial benefits, along with the absorbency benefit, when applied to a nonwoven fabric such as that which would be used as an absorbent pad in an adhesive bandage, or as a perforated barrier layer between the absorbent pad and the wound site.

Although various embodiments of the invention have been described using specific terms, devices, and methods, such description is for illustrative purposes only. The words are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A bandage of the type used on acute wounds, burn wounds and irritations comprising:
    a first layer for covering a wound site and an area around the wound site, said first layer including a top surface and bottom surface;
    a second layer over said first layer bottom surface, for absorbing exudates from the wound site; said second layer including a crosslinked poly(ethyleneoxide)-based resin that has been modified by grafting with an alkoxy silane functional group and a chitosan-based compound, and wherein at least one wound healing antimicrobial agent is associated with the bandage in a position where said wound healing antimicrobial agent will come in contact with the wound site, and which is transferable from the bandage to the wound site, upon contact with the wound site.

2. The bandage of claim 1, wherein said concentration of said resin is between about 0.1 and 6 weight percent in solution.

3. The bandage of claim 2, wherein said concentration of said resin is between about 0.1 and 4 weight percent in solution.

4. The bandage of claim 1 wherein said bandage is an adhesive bandage wherein an adhesive layer for adhesively bonding the bandage to a wound site is positioned between said first layer and said second layer.

5. The bandage of claim 1 wherein said wound healing antimicrobial agent is selected from niacinamide ascorbate and Chitosan niacinamide ascorbate.

6. The bandage of claim 1, wherein said wound healing antimicrobial agent is situated in or on the second layer.

7. The bandage of claim 1 wherein the second layer is a film.

8. The bandage of claim 1 wherein the second layer is a fibrous material.

9. The bandage of claim 1 wherein the second layer is either a film or fibrous material that has been coated with the poly(ethylene oxide)-based material and chitosan based material.

10. The bandage of claim 1 further including a perforated anti-stick film layer over said second layer.

11. The bandage of claim 10, wherein said perforated anti-stick film layer is treated with a wound healing antimicrobial material that is transferable to a wound site.

12. A bandage of the type used on acute wounds, burn wounds and irritations comprising:
    a first layer for covering the wound site and an area around the wound site, said first layer including a top surface and bottom surface;
    a second layer over said first layer, bottom surface, for absorbing exudates from the wound site; said second layer including a poly(ethyleneoxide)-based compound that has been modified by grafting with an alkoxy silane functional group and a chitosan-based compound,
    a third layer over said second layer, said third layer being of a perforated anti-stick film layer, and wherein, at least one wound healing antimicrobial agent is associated with the bandage in a position where said wound healing antimicrobial agent will come in contact with the wound site, and which is transferable from the bandage to the wound site, upon contact with the wound site.

13. The bandage of claim 12 further including an adhesive layer between said first layer and said second layer, for adhesively bonding the bandage to a wound site.

14. The bandage of claim 12 wherein said wound healing antimicrobial agent is selected from niacinamide ascorbate and Chitosan niacinamide ascorbate.

15. The bandage of claim 12 wherein said wound healing antimicrobial agent situated on the perforated anti-stick film layer.

16. The bandage of claim 1 wherein said chitosan in the bandage is between about 0.01 and 75% of the second layer.

17. The bandage of claim 1 wherein the range of wound healing antimicrobial agent is between about 0.1 and 70% by weight of the second layer.

* * * * *

UNITED STATES PATENT AND TRADEMARK OFFICE
CERTIFICATE OF CORRECTION

| | | |
|---|---|---|
| PATENT NO. | : 6,967,261 B1 | Page 1 of 1 |
| APPLICATION NO. | : 10/034906 | |
| DATED | : November 22, 2005 | |
| INVENTOR(S) | : David Allen Soerens and Sohail Malik | |

It is certified that error appears in the above-identified patent and that said Letters Patent is hereby corrected as shown below:

Column 40, line 59, "a first layer for covering a wound site and an area around" should be --"a first layer for covering the wound site and an area around"--
Column 41, line 14, "adhesive bandage wherein an adhesive layer for adhesively" should be --"adhesive bandage, and wherein an adhesive layer for adhesively"--

Signed and Sealed this

Thirtieth Day of January, 2007

JON W. DUDAS
*Director of the United States Patent and Trademark Office*